US008563919B2

(12) United States Patent
Coolens et al.

(10) Patent No.: US 8,563,919 B2
(45) Date of Patent: Oct. 22, 2013

(54) DYNAMIC FLOW IMAGING PHANTOM AND MODEL THEREFOR

(75) Inventors: Catherine Coolens, Toronto (CA); Harald Keller, Toronto (CA); Brandon Driscoll, Toronto (CA)

(73) Assignee: University Health Network, Toronto (CA)

( * ) Notice: Subject to any disclaimer, the term of this patent is extended or adjusted under 35 U.S.C. 154(b) by 212 days.

(21) Appl. No.: 13/117,764

(22) Filed: May 27, 2011

(65) Prior Publication Data
US 2011/0293074 A1 Dec. 1, 2011

Related U.S. Application Data

(60) Provisional application No. 61/349,466, filed on May 28, 2010.

(51) Int. Cl.
*G01D 18/00* (2006.01)

(52) U.S. Cl.
USPC ............... 250/252.1; 434/268; 435/284.1

(58) Field of Classification Search
USPC ............... 250/252.1; 434/268; 435/284.1; 378/207
See application file for complete search history.

(56) References Cited

U.S. PATENT DOCUMENTS

| 5,362,622 | A | * | 11/1994 | O'Dell et al. | 435/284.1 |
| 5,583,902 | A | * | 12/1996 | Bae | 378/8 |
| 5,792,603 | A | * | 8/1998 | Dunkelman et al. | 435/1.2 |
| 5,846,828 | A | * | 12/1998 | Peterson et al. | 435/399 |
| 6,100,082 | A | * | 8/2000 | Hassanein | 435/284.1 |
| 6,121,042 | A | * | 9/2000 | Peterson et al. | 435/284.1 |
| 6,629,469 | B2 | | 10/2003 | Jaszczak et al. | |
| 7,288,759 | B2 | | 10/2007 | Frangioni et al. | |
| 2003/0129736 | A1 | * | 7/2003 | Mitrani | 435/284.1 |
| 2004/0236216 | A1 | | 11/2004 | Manjeshwar et al. | |
| 2005/0277912 | A1 | * | 12/2005 | John | 604/890.1 |
| 2007/0231783 | A1 | * | 10/2007 | Prabhakarpandian et al. | 435/4 |
| 2007/0243523 | A1 | * | 10/2007 | Ionescu-Zanetti et al. | 435/4 |
| 2008/0293135 | A1 | * | 11/2008 | Orr et al. | 435/357 |
| 2009/0121712 | A1 | * | 5/2009 | Han et al. | 324/307 |

(Continued)

FOREIGN PATENT DOCUMENTS

| EP | 1222627 B1 | 8/2008 |
| WO | 2008130380 A2 | 10/2008 |
| WO | 2010089699 A2 | 8/2010 |

OTHER PUBLICATIONS

Authors: J. Rodney Levick1 and C. Charles Michel 2, Title: Microvascular fluid exchange and the revised Starling principle, Date: Mar. 3, 2010, Publisher: European Society of Cardiology.*

(Continued)

*Primary Examiner* — David Porta
*Assistant Examiner* — Taeho Jo
(74) *Attorney, Agent, or Firm* — Norton Rose Fulbright Canada LLP

(57) ABSTRACT

A phantom for simulation of perfusion, for use in dynamic flow imaging. The phantom includes a first compartment having a first inlet and a first outlet, and a second compartment having a second outlet. The first and the second compartments have fluid communication with each other, to simulate perfusion between the first and the second compartments. The first and the second outlets are separately controllable to adjust outflow of fluid from each compartment and to adjust fluid pressure in each compartment, thereby controlling rates of communication of fluids between the first and the second compartments.

12 Claims, 32 Drawing Sheets

(56) References Cited

U.S. PATENT DOCUMENTS

| | | | |
|---|---|---|---|
| 2009/0316972 | A1 | 12/2009 | Borenstein et al. |
| 2010/0030073 | A1 | 2/2010 | Kalafut |
| 2010/0318025 | A1* | 12/2010 | John ............................ 604/84 |
| 2011/0190680 | A1* | 8/2011 | Vodovotz et al. ............ 604/6.09 |
| 2012/0183987 | A1* | 7/2012 | Gevaert et al. .................. 435/29 |

OTHER PUBLICATIONS

Authors: Bauer WR, Hiller KH, Roder F, Rommel E, Ertl G, Haase A., Title: Magnetization exchange in capillaries by microcirculation affects diffusion-controlled spin-relaxation: a model which describes the effect of perfusion on relaxation enhancement by intravascular contrast agents, Publisher:Magn Reson Med. Date: Jan. 1996.*

Huda W, Scalzetti EM, Levin G, "Technique factors and image quality as functions of patient weight at abdominal CT Radiology" 217 430-435, 2000.

Miles KA. "Perfusion CT for the assessment of tumour vascularity: which protocol?" Br J Radiol 2003;76 Spec No. 1: S36-42.

Axel L. "Cerebral blood flow determination by rapid-sequence computed tomography: theoretical analysis". Radiology 1980;137:679-686.

Blomley MJ, Coulden R, Bufkin C, et al. "Contrast bolus dynamic computed tomography for the measurement of solid organ perfusion". Invest Radiol 1993;28 Suppl 5:S72-77; discussion S78.

Blomley MJ, Dawson P. "Bolus dynamics: theoretical and experimental aspects". Br J Radiol 1997;70:351-359.

Miles KA. "Measurement of tissue perfusion by dynamic computed tomography". Br J Radiol 1991;64:409-412.

St Lawrence KS, Lee TY. "An adiabatic approximation to the tissue homogeneity model for water exchange in the brain: I. Theoretical derivation". J Cereb Blood Flow Metab 1998;18:1365-1377.

Cenic A, Nabavi DG, Craen RA, et al. "Dynamic CT measurement of cerebral blood flow: a validation study". AJNR Am J Neuroradiol 1999;20:63-73.

Cenic A, Nabavi DG, Craen RA, et al. "A CT method to measure hemodynamics in brain tumors: validation and application of cerebral blood flow maps". JNR Am J Neuroradiol 2000;21:462-470.

Koh TS, Zeman V, Darko J, et al. "The inclusion of capillary distribution in the adiabatic tissue homogeneity model of blood flow". Phys Med Biol 2001;46:1519-1538.

Koh TS, Markus Tan CK, Dennis Cheong LH, and Tchoyoson Lim CC. "Cerebral perfusion mapping using a robust and efficient method for deconvolution analysis of dynamic contrast-enhanced images". NeuroImage 32 643-653, 2006.

Folkman J. "What is the evidence that tumors are angiogenesis dependent?" J Natl Cancer Inst 1990;82:4-6.

Rajendran JG, Krohn KA. "Imaging hypoxia and angiogenesis in tumors". Radiol Clin North Am 2005;43:169-187.

Jain RK. "Barriers to drug delivery in solid tumors". Sci Am 1994;271:58-65.

Jain RK. "Determinants of tumor blood flow: a review". Cancer Res 1988;48:2641-2658.

Videtic GM, Belderbos JS, Spring Kong FM, et al. "Report from the International Atomic Energy Agency (IAEA) consultants' meeting on elective nodal irradiation in lung cancer: small-cell lung cancer (SCLC)". Int J Radiat Oncol Biol Phys 2008;72:327-334.

Haasbeek CJ, Slotman BJ, Senan S. "Radiotherapy for lung cancer: Clinical impact of recent technical advances". Lung Cancer 2009.

Roy AE, Wells P. "Volume definition in radiotherapy planning for lung cancer: how the radiologist can help. Cancer Imaging 2006";6:116-123.

Daisne JF, Gregoire V. "Multimodalities imaging for target volume definition in radiotherapy". Bull Cancer 2006;93:1175-1182.

Halpin SF. "Brain imaging using multislice CT: a personal perspective. British Journal of Radiology" 2004;77 Spec No. 1:S20-26.

Park I, Tamai G, Lee MC, et al. "Patterns of recurrence analysis in newly diagnosed glioblastoma multiforme after three-dimensional conformal radiation therapy with respect to pre-radiation therapy magnetic resonance spectroscopic findings". Int J Radiat Oncol Biol Phys 2007;69:381-389.

Treuer H, Kocher M, Hoevels M, et al. "Impact of target point deviations on control and complication probabilities in stereotactic radiosurgery of AVMs and metastases". Radiother Oncol 2006;81:25-32.

Bolondi L, Gaiani S, Celli N, et al. "Characterization of small nodules in cirrhosis by assessment of vascularity: the problem of hypovascular hepatocellular carcinoma". Hepatology 2005;42:27-34.

Dawson LA, Brock KK, Kazanjian S, et al. "The reproducibility of organ position using active breathing control (ABC) during liver radiotherapy". 2001;51:1410-1421.

Dawson LA, Ten Haken RK, Lawrence TS. "Partial irradiation of the liver". Semin Radiat Oncol 2001;11:240-246.

Funama Y, Awai K, Miyazaki O, et al. "Improvement of low-contrast detectability in low-dose hepatic multidetector computed tomography using a novel adaptive filter: evaluation with a computer-simulated liver including tumors". 2006;41:1-7.

Padhani AR, Ollivier L. "The RECIST (Response Evaluation Criteria in Solid Tumors) criteria: implications for diagnostic radiologists". Br J Radiol 2001;74:983-986.

Miles KA, Charnsangavej C, Lee FT, et al. "Application of CT in the investigation of angiogenesis in oncology. Acad Radiol" 2000;7:840-850.

Tateishi U, Nishihara H, Watanabe S, et al. "Tumor angiogenesis and dynamic CT in lung adenocarcinoma: radiologic-pathologic correlation". J Comput Assist Tomogr 2001;25:23-27.

Choi JB, Park CK, Park DW, et al. "Does contrast enhancement on CT suggest tumor response for chemotherapy in small cell carcinoma of the lung?" J Comput Assist Tomogr 2002;26:797-800.

Sahani DV, Kalva SP, Hamberg LM, et al. "Assessing tumor perfusion and treatment response in rectal cancer with multisection CT: initial observations". Radiology 2005;234:785-792.

Hermans R, Meijerink M, Van Den Bogaert W, et al. "Tumor perfusion rate determined noninvasively by dynamic computed tomography predicts outcome in head-and-neck cancer after radiotherapy". Int J Radiat Oncol Biol Phys 2003;57:1351-1356.

Millar BA, Purgie TG, Yeung I, et al. "Assessing perfusion changes during whole brain irradiation for patients with cerebral metastases". J Neurooncol 2005;71:281-286.

Henderson E, Milosevic MF, Haider MA, et al. "Functional CT imaging of prostate cancer". Phys Med Biol 2003;48:3085-3100.

Ma SH, Xu K, Xiao ZW, et al. "Peripheral lung cancer: relationship between multi-slice spiral CT perfusion imaging and tumor angiogenesis and cyclin D1 expression". Clinical Imaging 2007;31:165-177.

Kiessling F, Boese J, Corvinus C, et al. "Perfusion CT in patients with advanced bronchial carcinomas: a novel chance for characterization and treatment monitoring?" Eur Radiol 2004;14:1226-1233.

Haider MA, Milosevic M, Fyles A, et al. "Assessment of the tumor microenvironment in cervix cancer using dynamic contrast enhanced CT, interstitial fluid pressure and oxygen measurements". Int J Radiat Oncol Biol Phys 2005;62:1100-1107.

Harvey CJ, Blomley MJ, Dawson P, et al. "Functional CT imaging of the acute hyperemic response to radiation therapy of the prostate gland: early experience". Journal of Computer Assisted Tomography 2001;25:43-49.

Harvey C, Dooher A, Morgan J, et al. "Imaging of tumour therapy responses by dynamic CT". Eur J Radiol 1999;30:221-226.

Bondestam S, Halavaara JT, Jaaskelainen JE, et al. "Perfusion CT of the brain in the assessment of flow alterations during brachytherapy of meningioma". Acta Radiol 1999;40:469-473.

Roberts HC, Dillon WP. MR imaging of brain tumors: toward physiologic imaging. AJNR Am J Neuroradiol 2000;21:1570-1571.

Roberts HC, Roberts TP, Brasch RC, et al. "Quantitative measurement of microvascular permeability in human brain tumors achieved using dynamic contrast-enhanced MR imaging: correlation with histologic grade". AJNR Am J Neuroradiol 200021:891-899.

(56) References Cited

OTHER PUBLICATIONS

Roberts HC, Roberts TP, Bollen AW, et al. "Correlation of microvascular permeability derived from dynamic contrast-enhanced MR imaging with histologic grade and tumor labeling index: a study in human brain tumors". Acad Radiol 2001;8:384-391.

Roberts HC, Roberts TP, Ley S, et al. "Quantitative estimation of microvascular permeability in human brain tumors: correlation of dynamic Gd-DTPA-enhanced MR imaging with histopathologic grading". Acad Radiol 2002;9 Suppl 1:S151-155.

Kassner A, Roberts TP. "Beyond perfusion: cerebral vascular reactivity and assessment of microvascular permeability". Top Magn Reson Imaging 2004;15:58-65.

Kassner A, Roberts T, Taylor K, et al. "Prediction of hemorrhage in acute ischemic stroke using permeability MR imaging". AJNR Am J Neuroradiol 2005;26:2213-2217.

Lee Ksslat,Y. "An Adiabatic Approximation to the Tissue Homogeneity Model for Water Exchange in the Brain: II. Experimental Validation". Journal of Cerebral Blood Flow & Metabolism 1998:1378.

Roberts HC, Roberts TP, Smith WS, et al. "Multisection dynamic CT perfusion for acute cerebral ischemia: the "toggling-table" technique". AJNR Am J Neuroradiol 2001;22:1077-1080.

Kamena A, Streitparth F, Grieser C, et al. "Dynamic perfusion CT: optimizing the temporal resolution for the calculation of perfusion CT parameters in stroke patients". Eur J Radiol 2007;64:111-118.

Miles KA, Griffiths MR. "Perfusion CT: a worthwhile enhancement?" Br J Radiol 2003;76:220-231.

Miles KA, Griffiths MR, Fuentes MA. "Standardized perfusion value: universal CT contrast enhancement scale that correlates with FDG PET in lung nodules". Radiology 2001;220:548-553.

Seppenwoolde Y, Shirato H, Kitamura K, et al. "Precise and real-time measurement of 3D tumor motion in lung due to breathing and heartbeat, measured during radiotherapy". Int J Radiat Oncol Biol Phys 2002;53:822-834.

Miles KA, Young H, Chica SL, et al. "Quantitative contrast-enhanced computed tomography: is there a need for system calibration? Eur Radiol" 2007;17:919-926.

Asscher et al. (1965). "Capillary permeability to plasma proteins". Postgrad Med. J. 41:425434.

* cited by examiner

Table 1 * Indicates that pulsatile flow was generated by the perfusion pump following a 1 Hz wave form representing a human carotid function.

| Perfusion Pump Flow Rate (mL/s) | Injection Pump Flow Rate (mL/s) | Injection Time (s) | Valve Positions $V_{Cyl}:V_{Tube}$ (% Open) |
|---|---|---|---|
| 4.5 | 1.5 | 12 | 100:100 |
| 3.5* | 1 | 20 | 100:100 |
| 3.5* | 1 | 20 | 100:100 |
| 3.5* | 1 | 20 | 100:100 |
| 2.5 | 0.3 | 52 | 100:100 |
| 4.5* | 1.5 | 12 | 40:100 |
| 4.5* | 1.5 | 12 | 100:40 |

Table 2: Actual Iodine injected was 1411mg. Tissue retention time represents the time taken for the cylinder output to drop from its peak to half that value.

| Exp (#) | Calculated Total Injected (mg I) | Injection Peak Height (HU) | Cylinder Peak Height (HU) | Cylinder Retention Half-Life (s) | Total Output Peak Height (HU) |
|---|---|---|---|---|---|
| 1 | 2970.4 | 701 | 155.8 | 57.86 | 393 |
| 2 | 3050.2 | 701 | 158.2 | 53.28 | 399 |
| 3 | 3093.1 | 696 | 159.4 | 53.98 | 395 |
| μ | 3037.9 | 699.3 | 157.8 | 55.04 | 395.7 |
| σ | 62.29 | 2.89 | 1.83 | 2.46 | 3.05 |
| σ/μ | 2.05% | 0.41% | 1.16% | 4.48% | 0.77% |

FIG. 10

Table 3

| | $K_{trans}$ (mL g$^{-1}$ min$^{-1}$) | $K_{ep}$ (min$^{-1}$) | Initial Slope (HU sec$^{-1}$) | $v_e$ (%) |
|---|---|---|---|---|
| Liver Tissue | 0.418 | 1.945 | 4.03 | 21.5 |
| Phantom (mimicking output) | 1.147 | 2.541 | 4.41 | 45.1 |
| Phantom (mimicking input) | 0.309 | 0.762 | 2.05 | 40.5 |

Table 4

| | Brain | Phantom |
|---|---|---|
| Integral (HU s) | 948 | 1062 |
| Peak Height (HU) | 38 | 34 |
| Initial Slope (HU/s) | 2.53 | 1.89 |
| Retention Slope (HU/s) | -0.81 | -0.31 |

FIG. 11

Table 5: Summary of example Model Predictions versus example Experimental Results

| | Simple Step Function | | | Replica Liver Arterial Input | | | Replica Liver Tissue | | |
|---|---|---|---|---|---|---|---|---|---|
| | Model [Actual] | Result (±SD n=3) | Error (% ±SD) | Model | Result (±SD n=2) | Error (% ±SD) | Model | Result (±SD n=2) | Error (% ±SD) |
| Input Function Model | | | | | | | | | |
| Mass injected (mg) | 3012.8 [3000] | 3129±65.9 | 4.3±2.1 | 5259.8 [5311.8] | 5250.4±45.1 | 1.16±0.85 | 4557.2 [4616.2] | 4427.3±47.2 | 4.09±1.02 |
| Peak Height (HU) | 692.82 | 699±2.5 | 0.89±0.36 | 254.69 | 265.2±2.5 | 3.98±0.93 | 197.00 | 199.7±0.6 | 1.36±0.31 |
| Goodness of Fit ($R^2$) | - | - | 0.99±0.003 | - | - | 0.98±0.003 | - | - | 0.94±0.027 |
| Output Function Model | | | | | | | | | |
| Tube Out Peak Height (HU) | 692.82 | 697±1.7 | 0.6±0.25 | 254.68 | 264.4±0.7 | 3.65±0.27 | 197.00 | 198.7±1.4 | 0.84±0.69 |
| Tube Out Goodness of Fit ($R^2$) | - | - | 0.97±0.002 | - | - | 0.97±0.007 | - | - | 0.96±0.006 |
| Cylinder Peak Height (HU) | 158.7 | 159±3.6 | 0.2±2.4 | 93.31 | 90.9±0.3 | 2.64±0.32 | 96.36 | 94.6±1.4 | 1.85±1.47 |
| Cylinder Out - Goodness of Fit ($R^2$) | - | - | 0.96±0.014 | - | - | 0.99±0.002 | - | - | 0.99±0.005 |
| Total Out Peak Height (HU) | 415.31 | 395.3±3.2 | 5.1±0.8 | 178.42 | 173.9±2.4 | 2.57±1.36 | 136.11 | 131.0±1.1 | 3.90±0.83 |
| Total Out Goodness of Fit ($R^2$) | - | - | 0.92±0.004 | - | - | 0.97±0.008 | - | - | 0.98±0.010 |

FIG. 18

DYNAMIC FLOW IMAGING PHANTOM AND MODEL THEREFOR

CROSS-REFERENCE TO RELATED APPLICATIONS

The present disclosure claims priority from U.S. provisional patent application No. 61/349,466, filed May 28, 2010, the entirety of which is hereby incorporated by reference.

TECHNICAL FIELD

The present disclosure relates generally to imaging phantoms, in particular imaging phantoms for dynamic flow imaging and models therefor.

BACKGROUND

Advances in multi-slice Computed Tomography (CT) technology have enabled the increased utilization of Dynamic Contrast Enhanced (DCE) CT in a clinical setting. By cine scanning (i.e., obtaining time series images) at relatively short time intervals, tissue and vascular enhancement can be measured and tracked over time to give uptake curves from which the distribution of contrast agent in tissue can be modeled. Different parameter models for contrast material exchange have been developed, for example to quantify tissue perfusion, vascular permeability, and blood volume and plasma mean transit time[15, 22-28]. The term 'perfusion' may be used to refer to blood flow only, however 'perfusion CT' (pCT) may also be used to refer to the derivation of other functional parameters (e.g., as listed above) from conventional DCE-CT measurements. In the present disclosure, perfusion CT is used to refer to the use of CT for deriving flow parameters not limited to blood flow.

Perfusion CT may be used in various levels of cancer treatment, including, for example, from the staging & detection of disease[3-5], assessment of tumor micro-vascularity[1, 2], improved target definition, predict radiation-induced normal tissue damage after radiotherapy[6-10] and response to treatment[46]. An imaging method for perfusion studies has historically been MRI, which may provide a relatively large field-of-view (FOV). CT scanners have been developed allowing for wide-volumetric scans (e.g., as much as 16 cm in 350 msec). These 4D scanners may be useful over 2D dynamic scanners, for example where breathing induced anatomical motion can limit scan frequency and accuracy. This may offer the potential for relatively robust perfusion imaging which can tolerate a relative degree of motion. Furthermore, the potentially complex relationship between MRI signal and contrast kinetics and long acquisition times may be circumvented with CT, which may provide more simplicity in quantification through the relative linearity of CT enhancement to contrast concentration. X-ray therapy and diagnosis are used in management of cancer patients receiving radiation therapy (RT), where the risk associated with the additional radiation exposure from DCE-CT imaging may be factored differently. Additionally, the ability to add DCE-CT to conventional anatomical CT examinations, which may be commonly available and relatively low cost, may make DCE-CT useful for cancer therapy.

SUMMARY

In some aspects there is provided a phantom for simulation of perfusion, for use in dynamic flow imaging, the phantom comprising: a first compartment having a first inlet and a first outlet, the first inlet being connectable to fluid source for introducing fluid into the phantom; a second compartment having a second outlet; wherein the first and the second compartments have fluid communication with each other, to simulate perfusion between the first and the second compartments; each of the first and the second outlets being separately controllable to adjust outflow of fluid from each compartment and to adjust fluid pressure in each compartment, thereby controlling rates of communication of fluids between the first and the second compartments.

In some aspects there is provided a system for simulation of perfusion, for use in dynamic flow imaging, the system comprising: the phantom described above; a pump for providing fluid to the phantom; an injector for providing contrast to the fluid; and respective valves for controlling outflow from each of the first and the second outlets.

In some aspects there is provided a method of simulating perfusion in dynamic flow imaging using a phantom, the method comprising: providing the phantom described above; determining system parameters for controlling inflow and outflow of the phantom, to mimic a physiological condition; configuring outlet valves according to the determined system parameters; introducing a fluid into the phantom according to the determined system parameters; and imaging output from the phantom.

BRIEF DESCRIPTION OF THE DRAWINGS

Reference will now be made to the drawings, which show by way of example embodiments of the present disclosure, and in which:

FIG. 10 shows Tables 1 and 2 where Table 1 lists example experimental parameters utilized in example studies of the phantom and Table 2 lists results from an example comparison of replicate time concentration curves;

FIG. 11 shows Tables 3 and 7 where Table 3 lists results from an example comparison of perfusion parameters between a clinical liver and an example phantom mimicking the liver input or output and Table 4 lists results from an example comparison of perfusion between a clinical brain and an example phantom;

FIG. 18 illustrates Table 5 showing a comparison of results from an example model with results from an example phantom;

DETAILED DESCRIPTION

Figure 1:
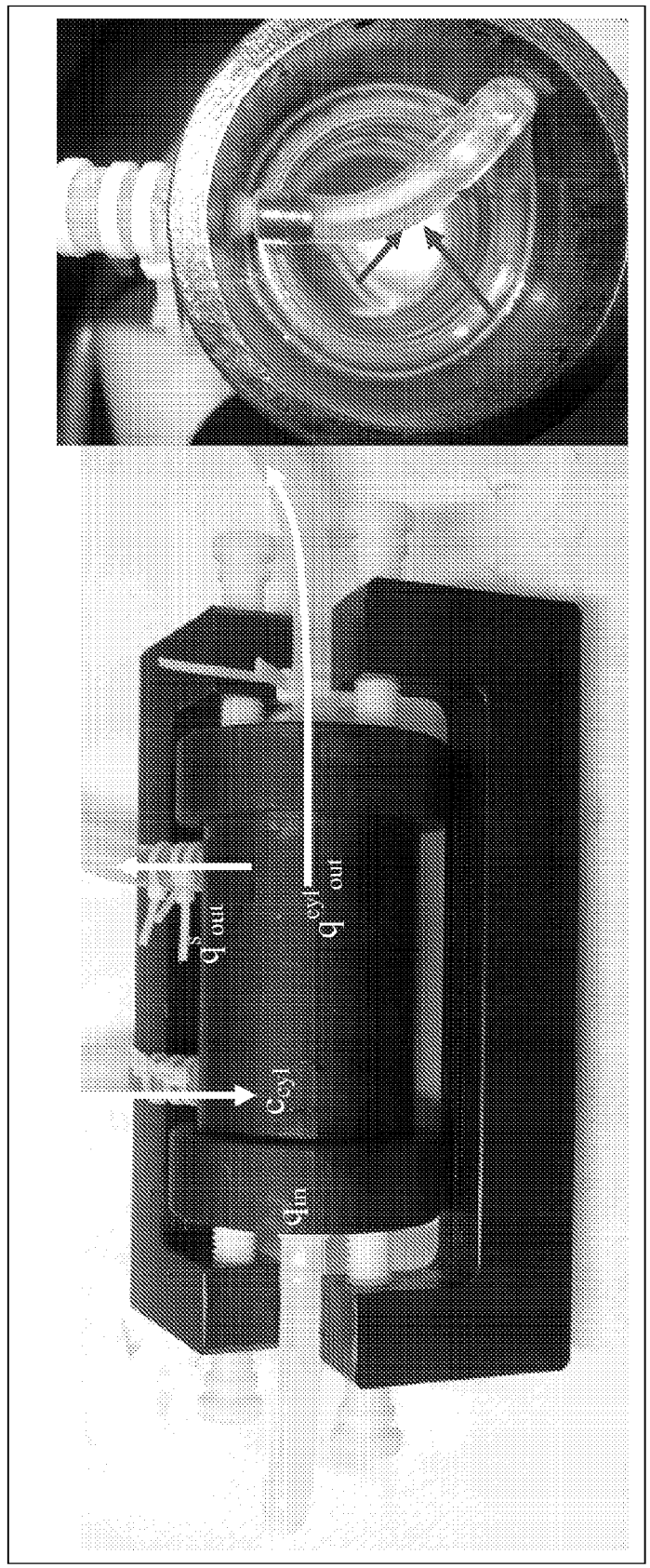
FIG. 1 shows an example phantom for dynamic flow imaging.

In the present disclosure, a dynamic flow imaging phantom is described. The phantom may be suitable for quantifying and/or validating DCE-CT measurements. This phantom, in some cases with its surrounding flow system, may be capable of creating a range of physiologically relevant time concentration curves which may be reproducible (e.g., with minimal error between experiments).

It may be desirable to address challenges in DCE-CT, including, for example, a need for calibration, difficulties in quantification, and motion induced artifacts. In radiation oncology, perfusion CT imaging may be applied, for example, for the purposes of target definition and evaluation of early treatment response, such as by quantitative measurement of changes in tumor neo-vascularisation. These measurements may be characterized by perfusion parameters which may be generated from one of a variety of perfusion models and which may provide comparable metrics such as tissue perfusion, vascular permeability, blood volume and plasma mean transit time[1-3]. Perfusion CT measurements may be modeled based on known kinetic models which provide perfusion parameters which can be used as comparable metrics between healthy and diseased tissue or organs[63-64]. However, it may be difficult to validate the many different kinetic models since they may be impacted by measurement uncertainties that arise from image artifacts and noise as well as under-sampling due to breathing or patient motion. It may be useful to calibrate the CT system for sensitivity to iodine in both relative and absolute terms to assess the stability of the calibration over time'.

A model for a dynamic flow imaging phantom is also disclosed. Using the disclosed model, experimental parameters (e.g., flow rate, output ratio, contrast injection bolus size and shape) can be chosen such that the phantom generates certain desired flow patterns, for example flow patterns similar to those of various different organs including brain, liver and lung, among others.

The model may also be applied in an optimization scheme to find experimental parameters to generate certain desired CT time concentration curves using the phantom. Such generated time concentration curves may be useful, for example, in QA applications or in the validation of kinetic models of perfusion.

The development of a dynamic flow imaging phantom may be useful, such as for creating a means of calibrating CT systems for DCE-CT. The additional application of creating physiologically relevant time concentration curves may be useful for validating perfusion models without the presence of organ motion, which may be challenging to achieve any other way. The disclosed phantom may be useful to create these time concentration curves. The disclosed model may be useful as a means of generating the desired system settings required in order to create the desired input and output curves using the phantom.

The disclosed model may be based at least partially on a two compartment model. The model may be able to predict both output functions based on an injection bolus and the settings of the flow system, such as the injection pump, flow control pump and flow control valve position. The model may take into account phantom parameters such as the input flow rates, valve positions, contrast concentration, bolus injection time and volume in order to predict the behaviour of the phantom.

The disclosed phantom and model may be used to predict the output of the phantom such that it can be used for quality assurance purposes with DCE-CT and/or to mimic clinical time concentration curves which can be utilized to quantify and/or validate kinetic models of perfusion CT.

In some examples, the phantom may provide reproducible results over a range of input and output flow functions. The phantom may provide a controllable input flow as well as a controllable ratio of the output flows. This may provide the ability to create a range of time concentration curves by adjusting the many different parameters available within the phantom and its flow system.

In some examples, the phantom may provide a tool for use in perfusion scanning protocols, which may help in improving image resolution and data acquisition while reducing the radiation dosage to the patient.

In some examples, the phantom may provide a means to test perfusion kinetics models without the movement induced by either breathing or patient motion while using known input and output time concentration curves which can be varied to suit the model.

Example Phantom

To assist in understanding the disclosed dynamic flow imaging phantom, consider example organs such as the liver and brain which are commonly observed with perfusion CT. In the liver, the perfusion analysis may be done by examining arterial input to the liver ($C_a$) and how that relates to the overall contrast level within the liver ($C_t$). Different parameter models for contrast material exchange have been developed to quantify tissue perfusion, vascular permeability, blood volume and plasma mean transit time[11-18].

For example, in the case of the liver the arterial input function typically provides a sharp bolus of contrast which lasts a matter of seconds before a reduction at the end of the peak which drops quickly before stabilizing to a slower decrease as the contrast is removed from the blood stream by the kidneys. The contrast levels in the liver itself typically vary depending on position and proximity to the hepatic artery where contrast enters the liver or the hepatic veins from which it exits.

To mimic such behaviour, the example phantom was based upon a two compartment kinetic model phantom. Other phantom designs (e.g., with more than two compartments) may be used. The two compartment model may be useful due to its relative simplicity and its familiarity.

The phantom may handle a range of input flow rates and produce multiple output flows, which may include one or more of the following properties:

A single flow in ($Q_{In}$) may be split into two output flows ($Q_{Out1}$ & $Q_{Out2}$).

The ratio of the two output flows may be variable and adjustable ($Q_{Out1}:Q_{Out2}$)

A contrast bolus may be added to the system to create a time concentration curve which can be tuned by adjusting the parameters of the system.

The phantom may be relatively robust and capable of functioning under physiologic or near physiologic flow.

The example phantom may be capable of producing a range of physiologically relevant time concentration curves. The phantom may be capable of producing relatively accurate and reproducible results which may provide a means to test perfusion kinetics models without the convolving contrast-enhancement measurement uncertainties that typically arise from image artifacts and noise as well as under-sampling due to breathing or patient motion. In this example, the flow system may create dynamic physiologically relevant time concentration curves, while the example phantom may represents a two-compartmental exchange mechanism.

In this example, the phantom may include a first and a second compartment. The first compartment may have an inlet and an outlet. Fluid (e.g., a blood-mimicking fluid and contrast agent) may be introduced into the phantom via the inlet. For example, the inlet may be connectable to pump for providing pulsatile fluid into the phantom. The second compartment may also have an outlet. The first and second compartments may exchange fluid with each other, for example via multiple communication orifices. This communication of fluid between compartments may mimic physiological perfusion. Fluid may be collected from the outlets of the two compartments and imaged. For example, the collected fluid may be imaged using DCE-CT. Each outlet may be separately controlled (e.g., using valves) to adjust the outflow of fluid from each compartment, thus adjusting the fluid pressure in each compartment. This may control the fluid communication between the compartments, for example to mimic physiological conditions.

Other phantom models may be suitable, for example having more complex exchange mechanisms, which may be used for mimicking other physiological behaviour and/or other organs.

An example phantom is shown in FIG. 1. In this example, the phantom may be similar to a shell and tube heat exchanger. Instead of exchanging heat, mass (e.g., fluid) may be exchanged from one compartment (e.g., the tube) to the other (e.g., the shell). In this example, the shell of the phantom may be a cylinder with two end caps with 2 inputs and 2 outputs (FIG. 1, Left). The tube may be directly connected to one inlet and one outlet of the cylinder, such that the tube provides the main inlet and outlet of the phantom, indicated by $q_{in}$ and $q_{out}^S$, respectively. The cylinder may have an optional inlet (e.g., to model dual input of a liver), indicated by $c_{cyl}$, and an outlet, indicated by $q_{out}^{cyl}$.

In this example, the tube has a multiple small holes to exchange mass (in this case, fluid) with the cylinder compartment. The tube may be made of a relatively flexible material (e.g., vinyl tubing), which may be removable and which may have variable properties including, for example, the tube length, number of turns, hole size, and number of holes (e.g., indicated by arrows in FIG. 1, Right). This may allow the phantom to be modified for mimicking different physiological behaviours. In this example, the tubing is 1/8" vinyl tubing and is 100 cm in length with 5 sets of 2 1.2 mm diameter holes.

Figure 2:
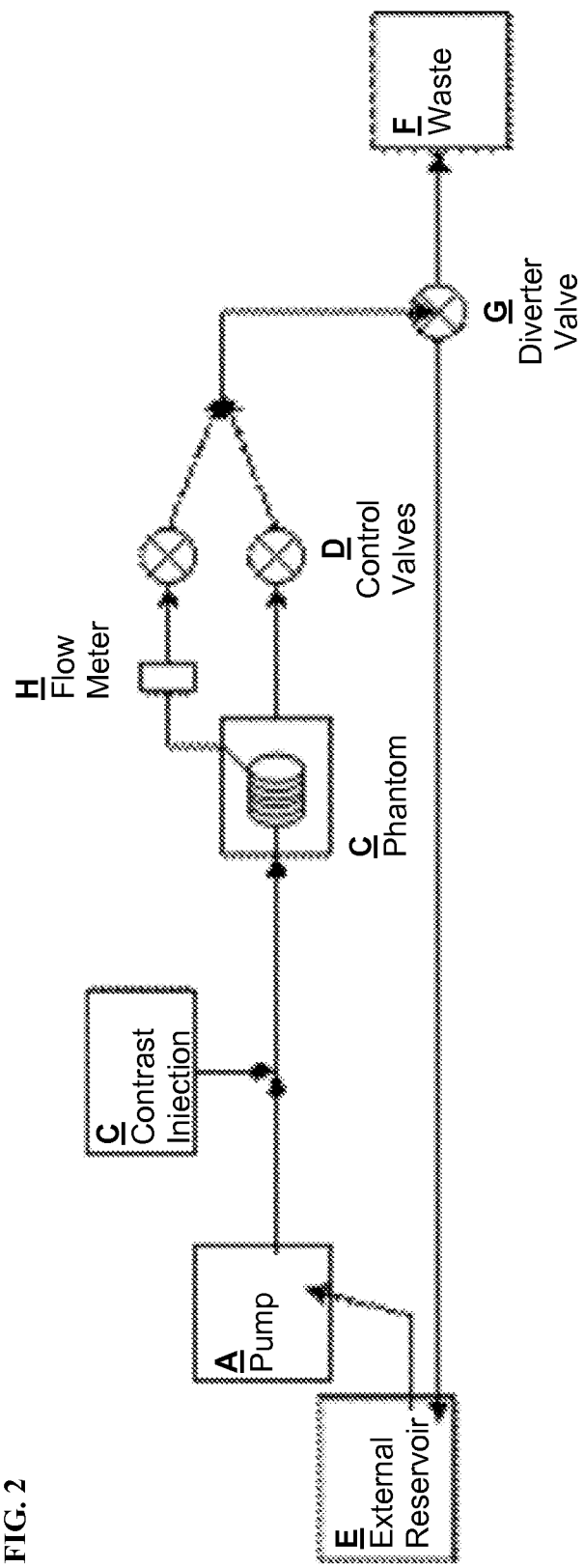
FIG. 2 is a schematic diagram of an example phantom for dynamic flow imaging.

The phantom may be used as part of a flow system. An example flow system is schematically shown in FIG. 2. In this example, the flow system may include a pump A, a mechanism for contrast injection B, the phantom C and control valves D. The system may also include reservoir tanks and connections (e.g., tubing) between components. The pump may be pulsatile pump. It should be understood that in some other example embodiments, the flow system may include more or less components than that described in this example. For example, the system may also include an external reservoir E to provide fluid for the pump A. The system may also include a waste receptacle F and a diverter valve G. The system may also include a flow meter H, for monitoring flow from the phantom.

In this example, the flow pump may be any suitable pump, such as a pulsatile flow positive displacement pump A, which may be capable of flow between 0.1 and 35 mL/s.

The flow control valves D placed on the cylinder and tube outputs, in this example, may be any suitable controllable valve, such as carbon steel needle valves (e.g., Deltrol Fluid Products, Bellwood, Ill.). These valves may be capable of a full range of control from fully open to fully closed. Should both valves be accidentally closed at any given time a pressure sensitive shutoff on the pump may be tripped, thus arresting the system before any damage is done to the phantom or the flow system. The valves may be controlled manually or using a processor.

In some examples, the dynamic flow phantom may be contained in a medium-filled container. For example, the phantom may be submerged and analyzed inside a water filled phantom. This may be useful for reducing or eliminating display artifacts (e.g., due to differences between imaging in air vs. imaging in liquid) and/or other sources of noise.

In some examples, contrast may be introduced into the system by injection, for example using a remote controlled syringe infusion pump C, in this example one capable of flow rates as low as 2 microliters per minute and up to 90 milliliters per minute using a standard 60 cc Becton Dickinson syringe. This example pump has the additional feature of being fully programmable allowing the generation of different shaped boluses or even a simple linear increase or decrease.

Example Studies

Figure 5A:
FIGS. 5A-5B shows an example setup for dynamic contrast enhancement imaging using an example phantom, and example results.
Figure 5B:
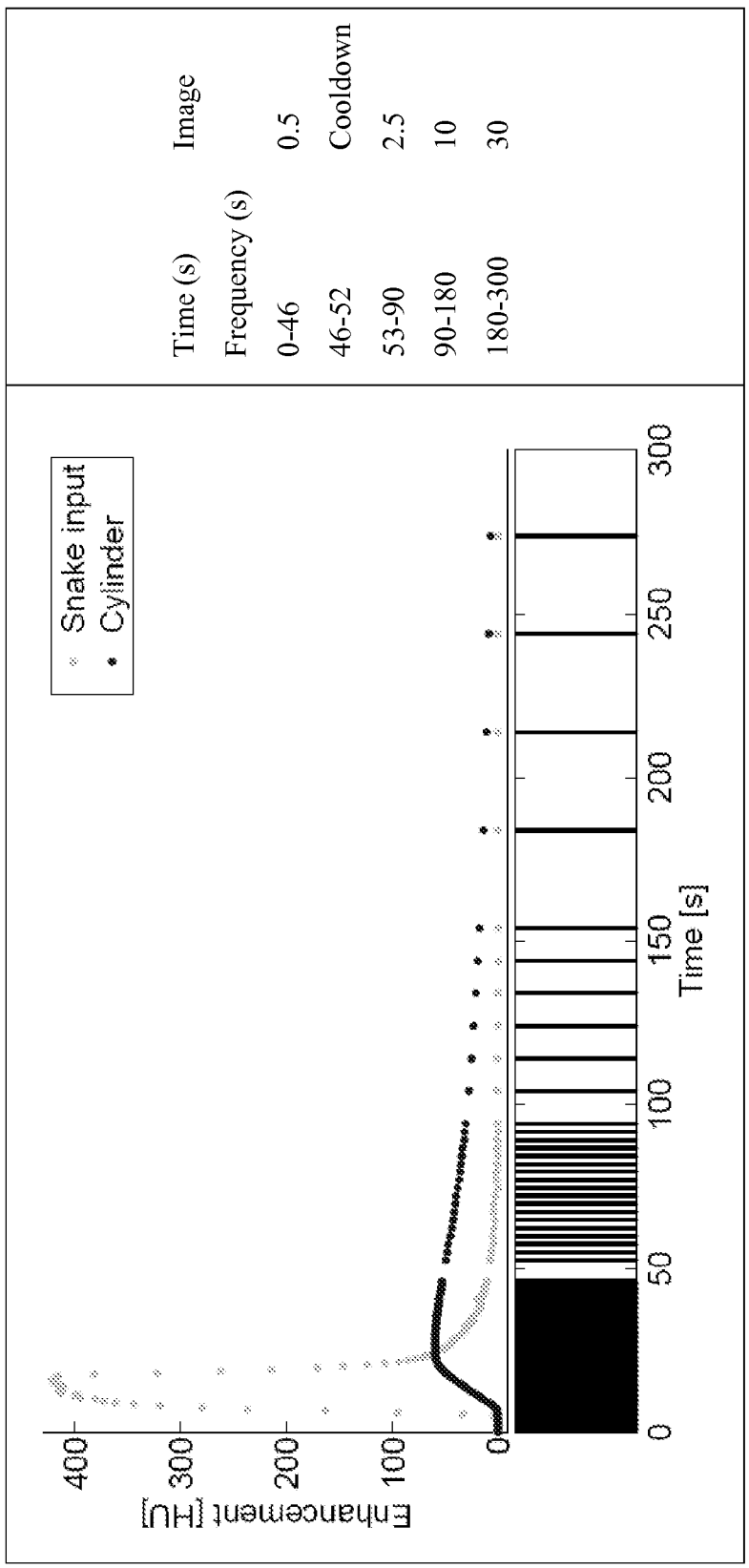

Example studies were carried out on the example phantom and system described above. The example phantom and syringe injection pump were placed directly on the bench of the scanner as shown in FIG. 5A. Imaging of the phantom was done with a conventional CT scanner. An example image frequency protocol used for the scanner is shown in FIG. 5B. The start of imaging coincided with the injection of contrast to the system.

Figure 6A:
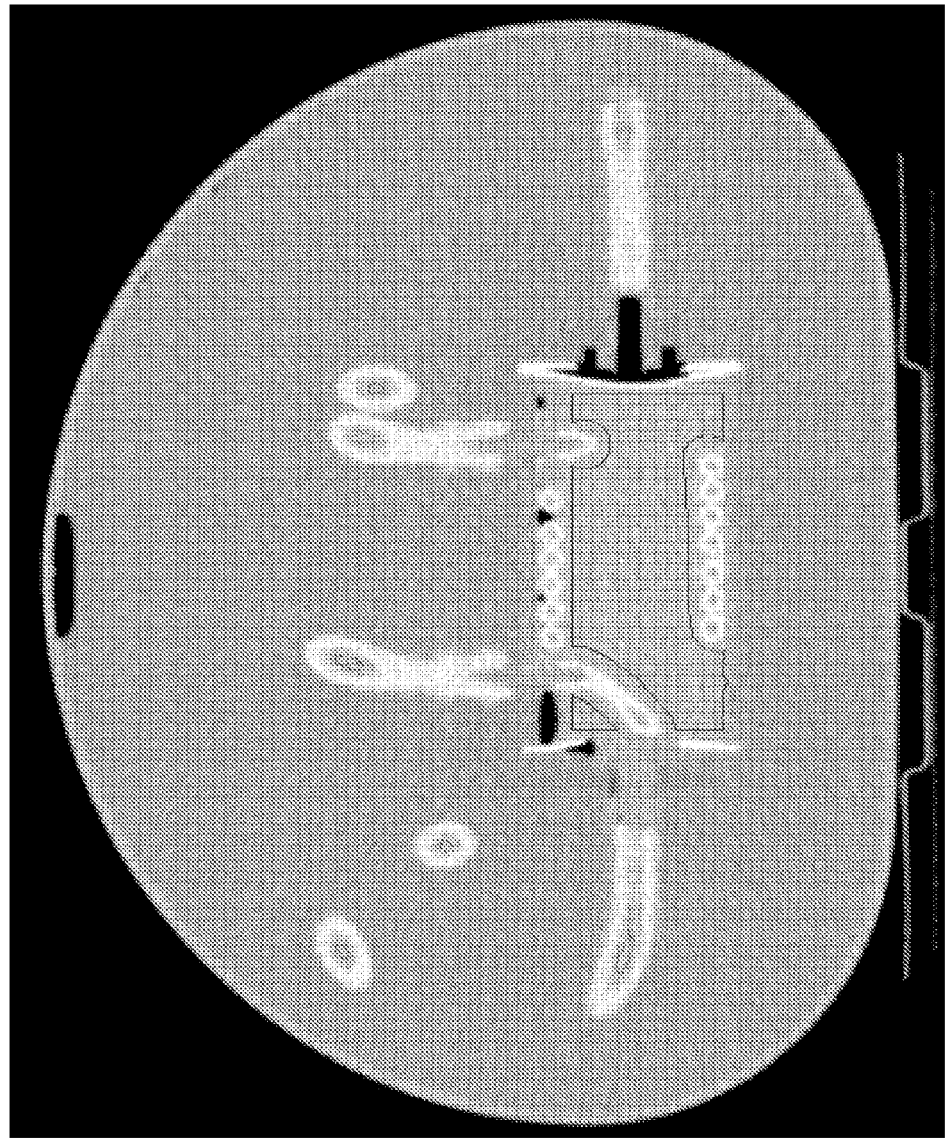
FIGS. 6A-6B shows an example of region of interest segmentation.
Figure 6B:
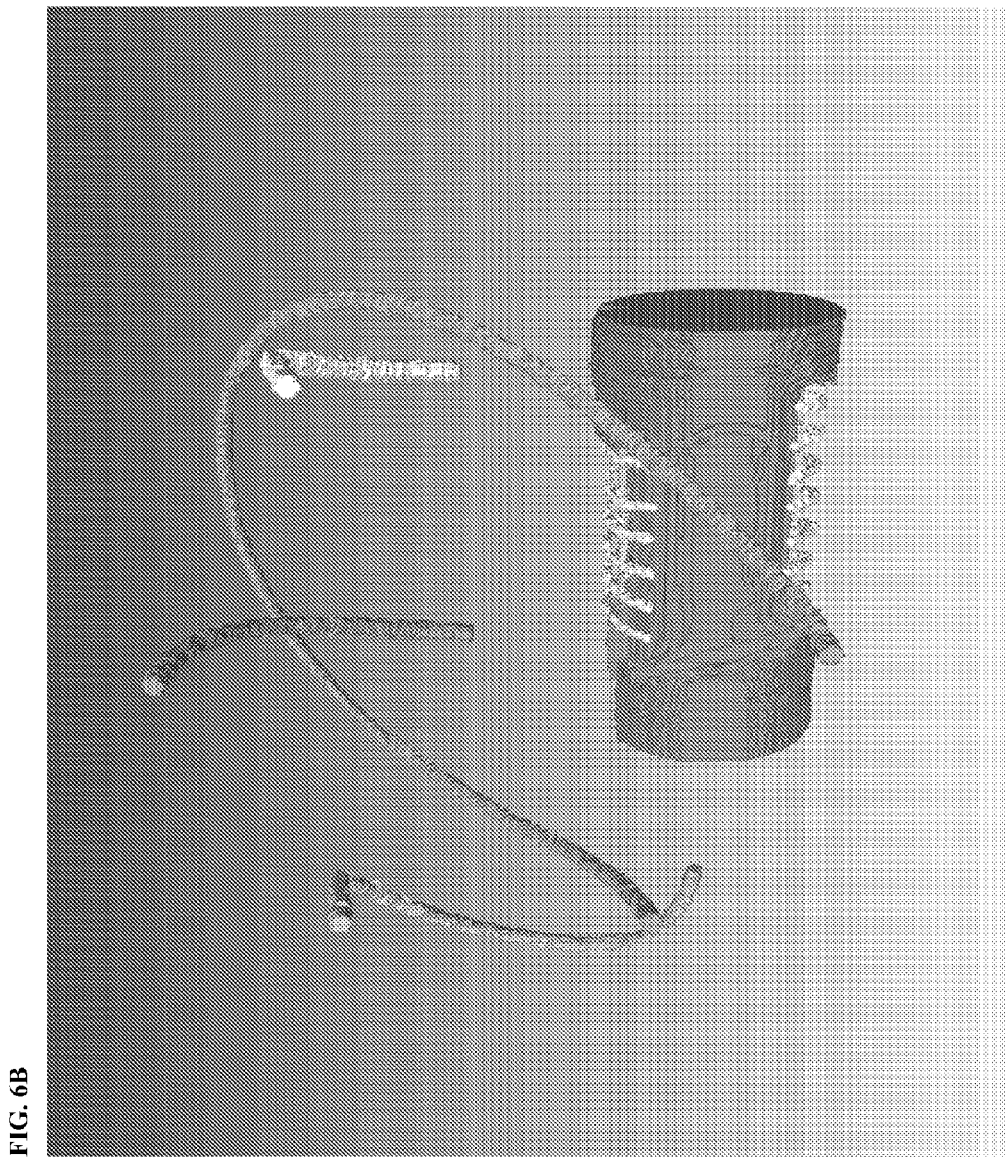

Image analysis of the obtained image time series included, in this example, a baseline raw image (e.g., the first time point) which was segmented into regions of interest (in this example, Flow In, Cylinder, Cylinder Out, Snake Out and Combined Out) (FIGS. 6A and 6B).

Segmentation of the image may be done using conventional methods, in this example, manually. A simple threshold based approach was not chosen as it may remove valid voxels from the first volume which may be low/high simply due to noise, leading to an artificially inflated (or deflated) value for the baseline when compared to the rest of the volume. The manual segmentation of the tubes was performed by drawing contours within the tubing with a radius of approximately half the actual tube inner radius. Though small in the axial plane (~10 voxels in diameter) the ROIs may still have a substantial volume as they are located on 100 or more slices which may reduce the noise in the measurements.

The mask file from the segmentation may be used to analyze the raw images of each time to compute the mean, maximum, minimum and standard deviation of each ROI for each time point.

Example studies were carried out on an example of the phantom, to assist in characterizing it with regards to a number of different properties, including the range of the phantom, its reproducibility and the effectiveness of the output valves with regards to altering the shape of the output curve. Table 1 in FIG. 10 displays the experimental parameters tested in the example studies.

The free parameters to produce various time concentration curves, in this example, are the Perfusion Pump Flow Rate ($Q_{Pump}$) the Injection Pump Flow Rate ($q_{Inject}$) the Injection Time ($t_{Inject}$) and the valve positions ($p_{Cyl}$:$p_{Tube}$) which control the ratio of the output flow rates ($q_{Cyl}$:$q_{Tube}$). For this study, the contrast (Visiopaque 270 mg/mL) concentration was diluted to 78.4 mg/mL (Exp 1, 5, 6, 7) or 150 mg/mL (exp 2-4).

In order to produce physiologically relevant time intensity curves it may be useful to determine experimental parameters to mimic the arterial input as well as the shape and intensity of the tissue curves. A method for determining such parameters may be using the phantom model disclosed herein and described further below. Following this approach, example clinical liver and brain tumour perfusion studies were carried out to generate suitable experimental parameters for their replication with the phantom.

The experimental parameters resulting from the example studied were compared to the clinical time intensity curves. Perfusion analysis using a Tofts kinetic model was performed on both the phantom and a clinical data set to establish the phantom's ability to represent human physiology. The parameters compared included: $K_{trans}$, transfer constant from vascular to interstitial compartment, $K_{ep}$, the reverse transfer constant, $v_e$ the interstitial volume fraction and the initial slope.

Figure 3A:
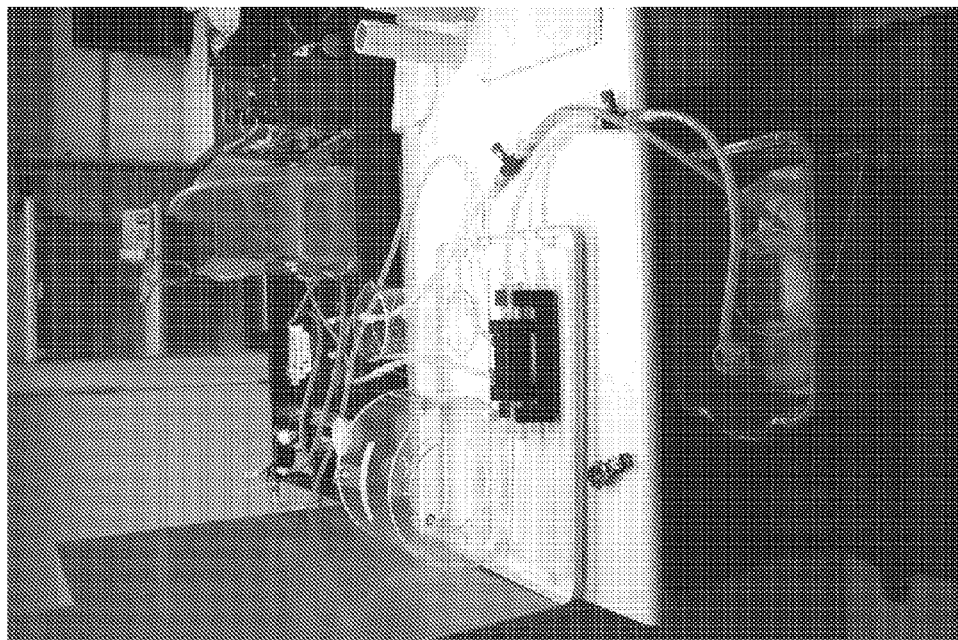
FIG. 3A shows an example setup for characterization of a phantom.
Figure 3B:
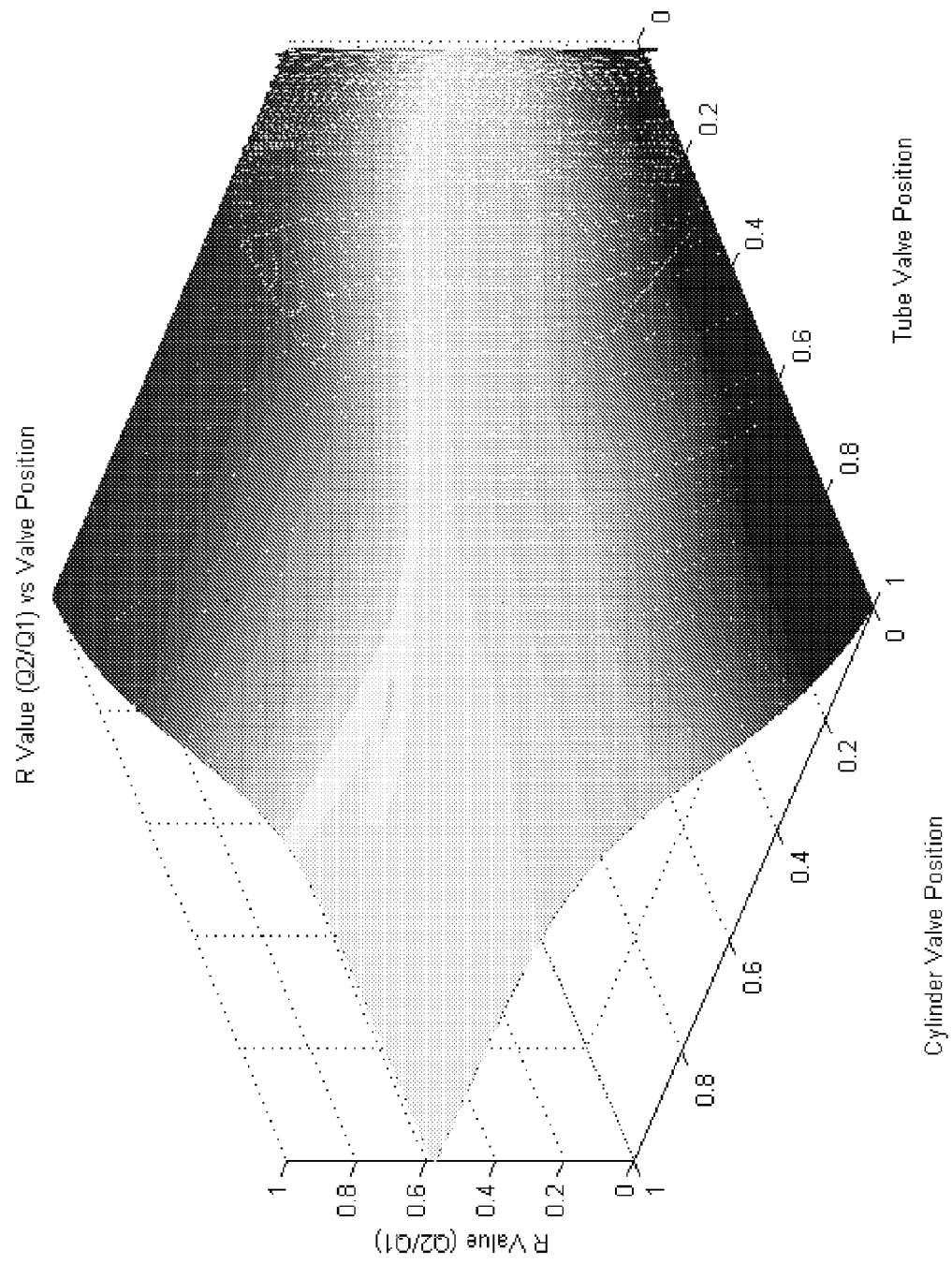
FIG. 3B shows a plot of example characterization results.

The example phantom was studied using a wide range of flow rates and valve positions. For each set up the output from the tubing and cylinder were measured independently over a sufficiently long time frame as to calculate an average flow rate using the apparatus shown in FIG. 3A. From this measured data it was possible to determine the relationship between valve position and output ratio at each flow rate. (FIG. 3B)

Using this example setup an output ratio R (defined as Flow Out of Cylinder/Total Flow In) of any value between 0 and 1 may be possible. In the fully open position the phantom (with the example tubing configuration described above) has an R value of approximately 0.5.

Figure 4A:
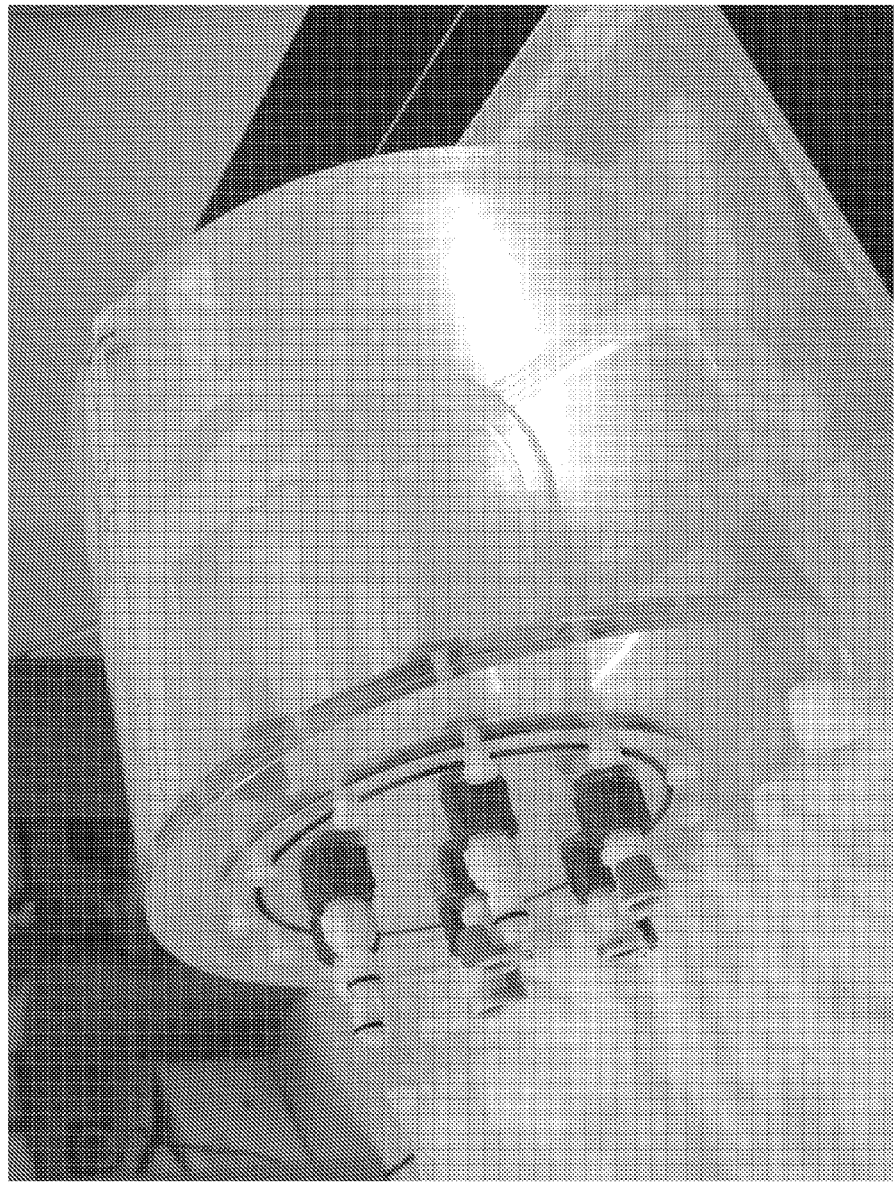
FIGS. 4A-4C shows an example of contrast calibration using an example phantom.
Figure 4B:
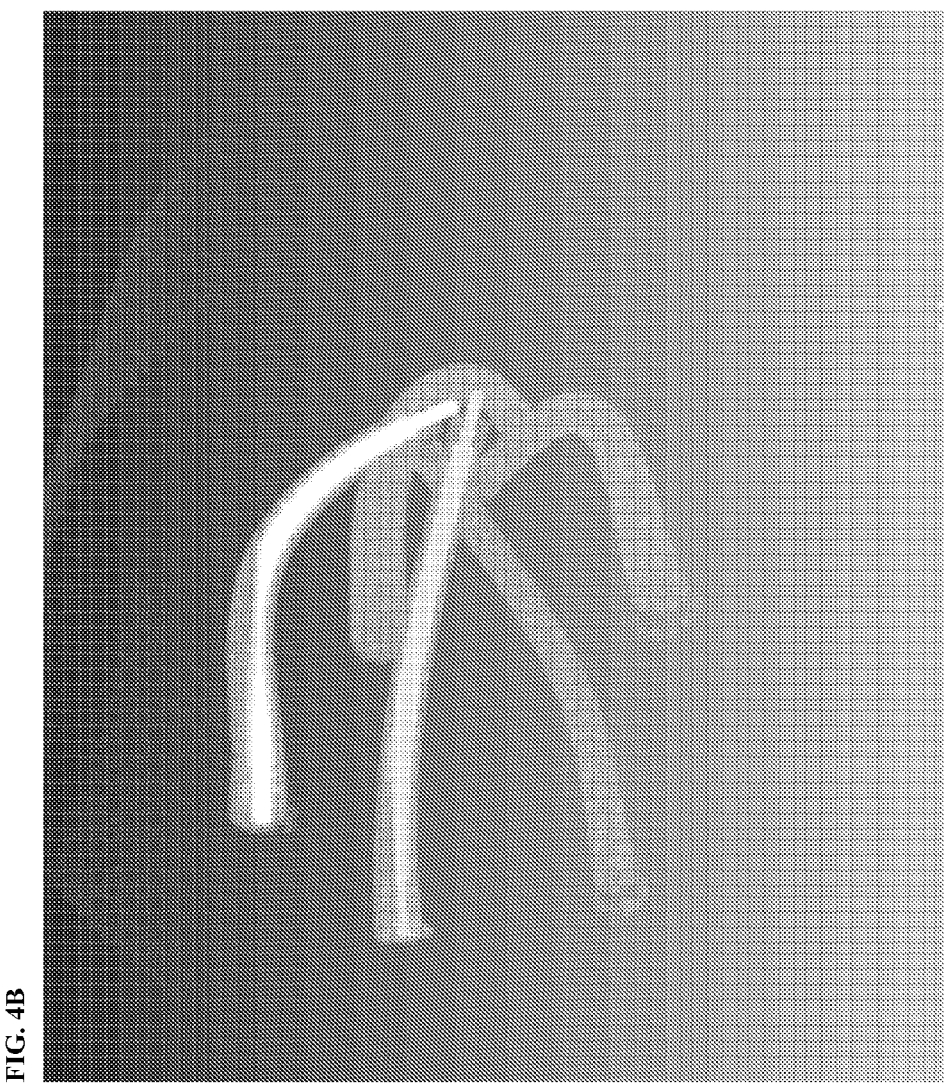
Figure 4C:
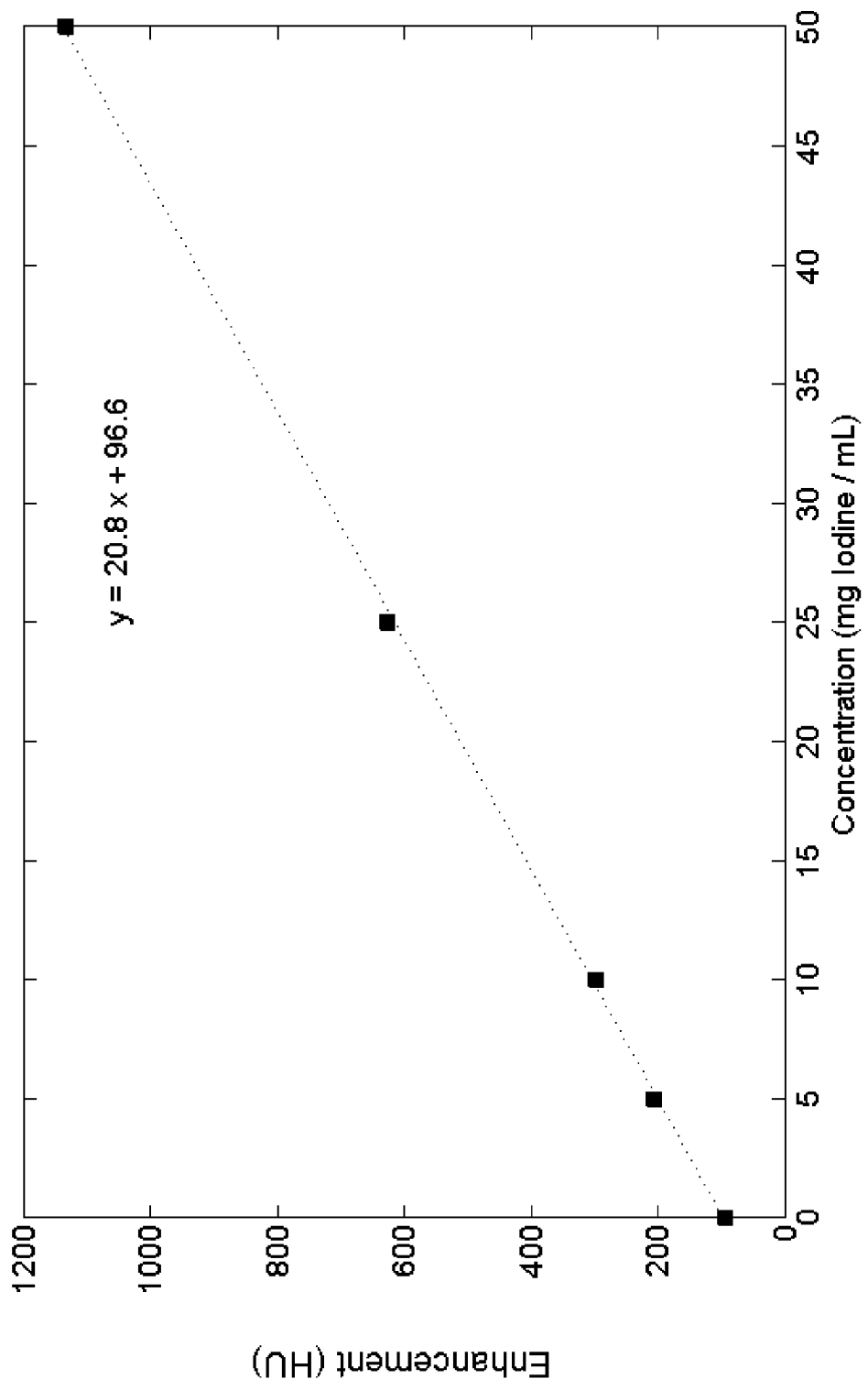

In this example, the "blood mimicking fluid" used by the pulsatile flow pump has a density of about 1.1 kg/L and has a CT number of approximately 100 HU. A contrast calibration curve for the contrast agent Visipaque™ (iodixanol) 270 mgI/mL (GE Healthcare, Canada) in the "blood mimicking fluid" was created by fabricating a basic contrast calibration phantom using the NEMA phantom and lid along with 5 sections of tubing with different concentrations of contrast (FIGS. 4A and 4B). By imaging the phantom, the enhancement of these tubes was used to create a contrast calibration curve allowing the conversion from CT numbers directly into a concentration for future analysis and modeling (FIG. 4C). The slope of the figure (20.8) represents the enhancement in terms of CT number per mg I/mL and the y-intercept (96.6) represents the CT number of the blood mimicking fluid.

Other DCE-CT experiments may be designed, for example for determining the range of different time concentration curves which could be generated with the phantom and also to perform replicate experiments for characterizing the run to run variability of the system.

For example, depending on the organ, a perfusion experiment can last anywhere from a few seconds, for example in the brain, to a number of minutes, for example in liver perfusion, or more. The initial input bolus may take on many forms, for example from a short sharp peak to a long rounded curve. In this example dynamic flow phantom the input pulse may be controlled, for example using a programmable injection pulse, and can be set to any suitable pulse, for example ranging from a simple step function to a complex series of peaks. The response of the example phantom to this input pulse can also be varied, for example by controlling the perfusion pump flow rates and/or the valves controlling the ratio of the output flows (e.g., the output from the cylinder and the tube).

Figure 7A:
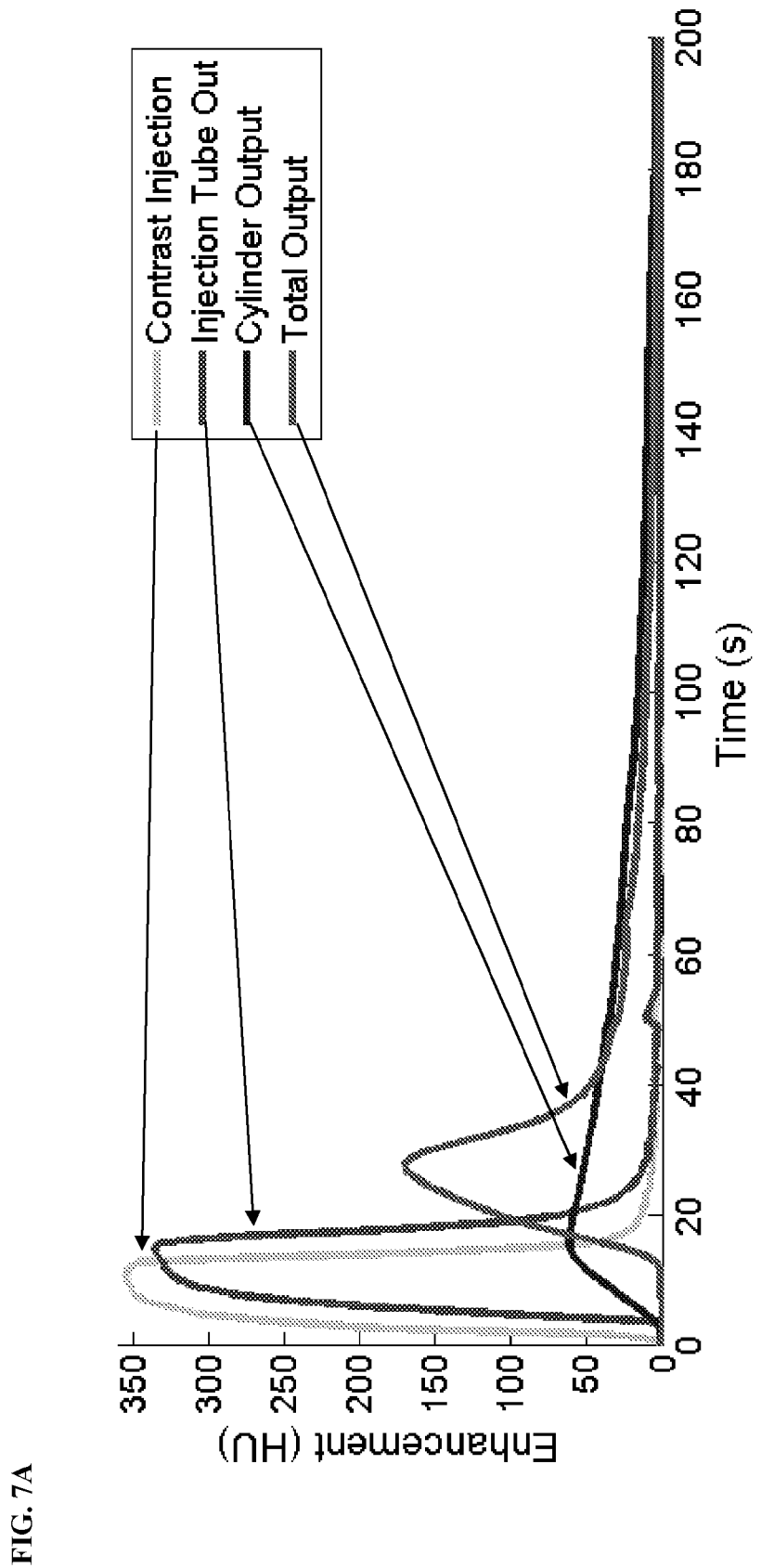
FIGS. 7A-7D shows example time concentration curves from example phantom characterizations.
Figure 7B:
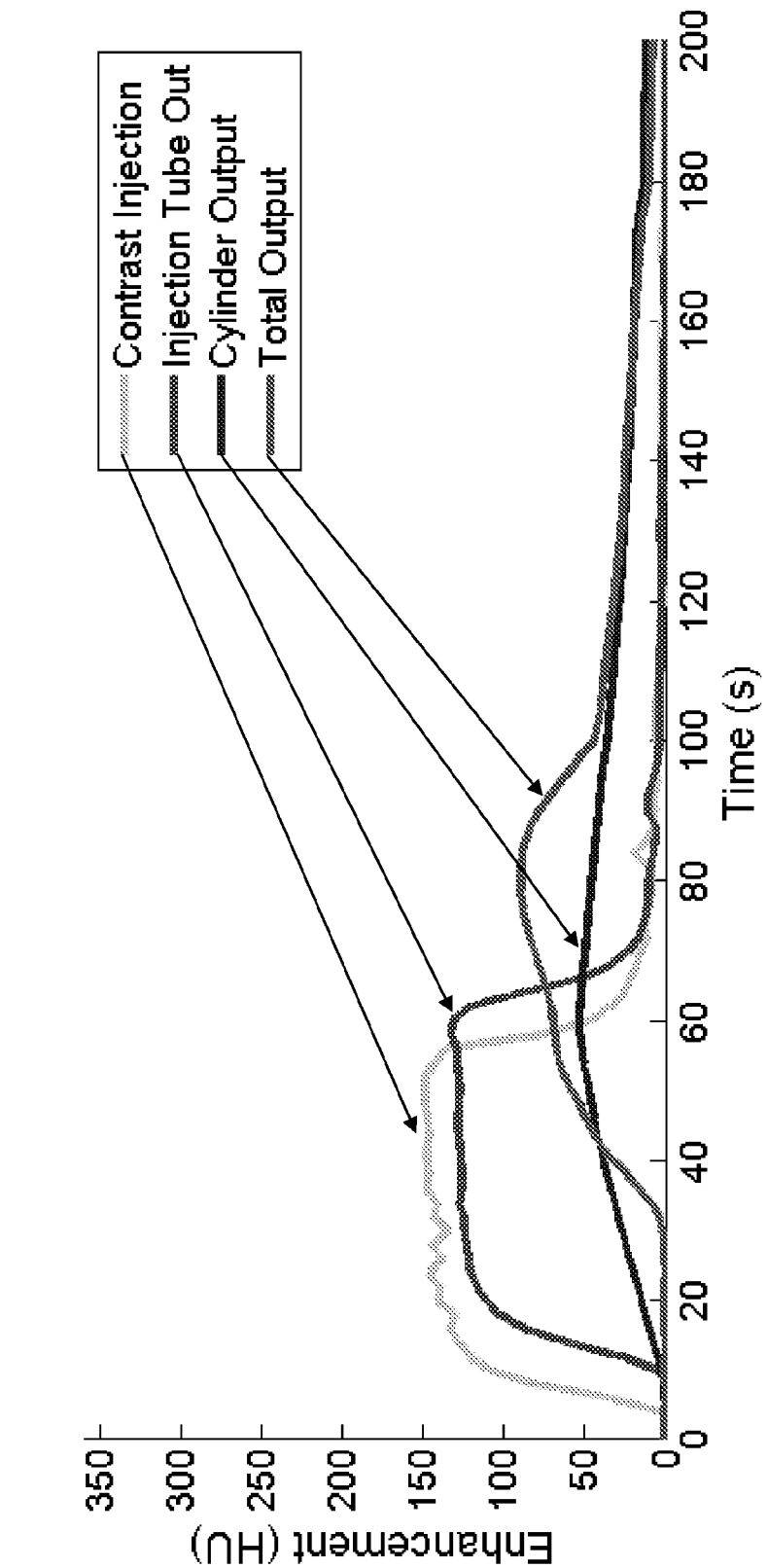

For example, experiments 1 & 5 demonstrate the difference in behaviour of the example phantom using a quick bolus (FIG. 7A) and a longer pulse (FIG. 7B). The quick bolus results in a rapid uptake of contrast in the cylinder (Initial Slope ($m_i$) of 2.45 HU/s) followed by its relatively fast expulsion (time to half max ($t_{1/2\ max}$) of 42.5 s) due to the increased flow rate (and s). As expected the slower input pulse results in a much more gradual uptake ($m_i$=1.08 HU/s) and eventual release from cylinder ($t_{1/2\ max}$=67 s).

The adjustment of the input curve may be an example method of altering the output curves from the phantom, another example method may be the adjustment of the flow control valves. For example, experiments 6 and 7 demonstrate the effects of closing either of the two valves. In experiment 6 (FIG. 7D) the valve controlling the cylinder compartment is closed 60% which increases the retention time of the contrast in the cylinder compartment but also reduces its maximum value ($m_i$=3.27 HU/s $t_{1/2\ max}$=71.8 s). Conversely in experiment 7 the adjustment of the valve controlling the tube output results in more contrast entering the cylinder but also a more rapid expulsion ($m_i$=4.26 HU/s, $t_{1/2\ max}$=49 s).

In this example, by controlling the flow control valves and/or programmable injection pulse, it may be possible to mimic a wide variety of different shaped injection and output time concentration curves, for example to mimic various physiological conditions.

To study reproducibility, the same experimental parameters were used on three separate occasions and on two different CT Scanners. Experiments 2 through 4 all used the same 20 second input step function pulse with the same perfusion pump flow rate (3.5 mL/s1 Hz carotid pulsatile flow). The resulting input and output time concentration curves (FIG. 7C) were then analyzed to compare the shape and intensity of the curves (see Table 2in FIG. 10).

In this example study, the input functions generated by the injection pump are very similar from run to run, for example varying by approximately 2% of the mean. A small spike at the top of the peak may be seen in Arterial Input 2. This peak and other similar ones observed in other experiments may be the result of the positive displacement flow pump reaching the end of a cycle and changing direction resulting in a slight deviation in the flow. The corresponding Tissue and Total Output peaks are similarly reproducible with the Tissue ½ retention time having the largest error at only 4.25% of the mean.

Figure 7C:
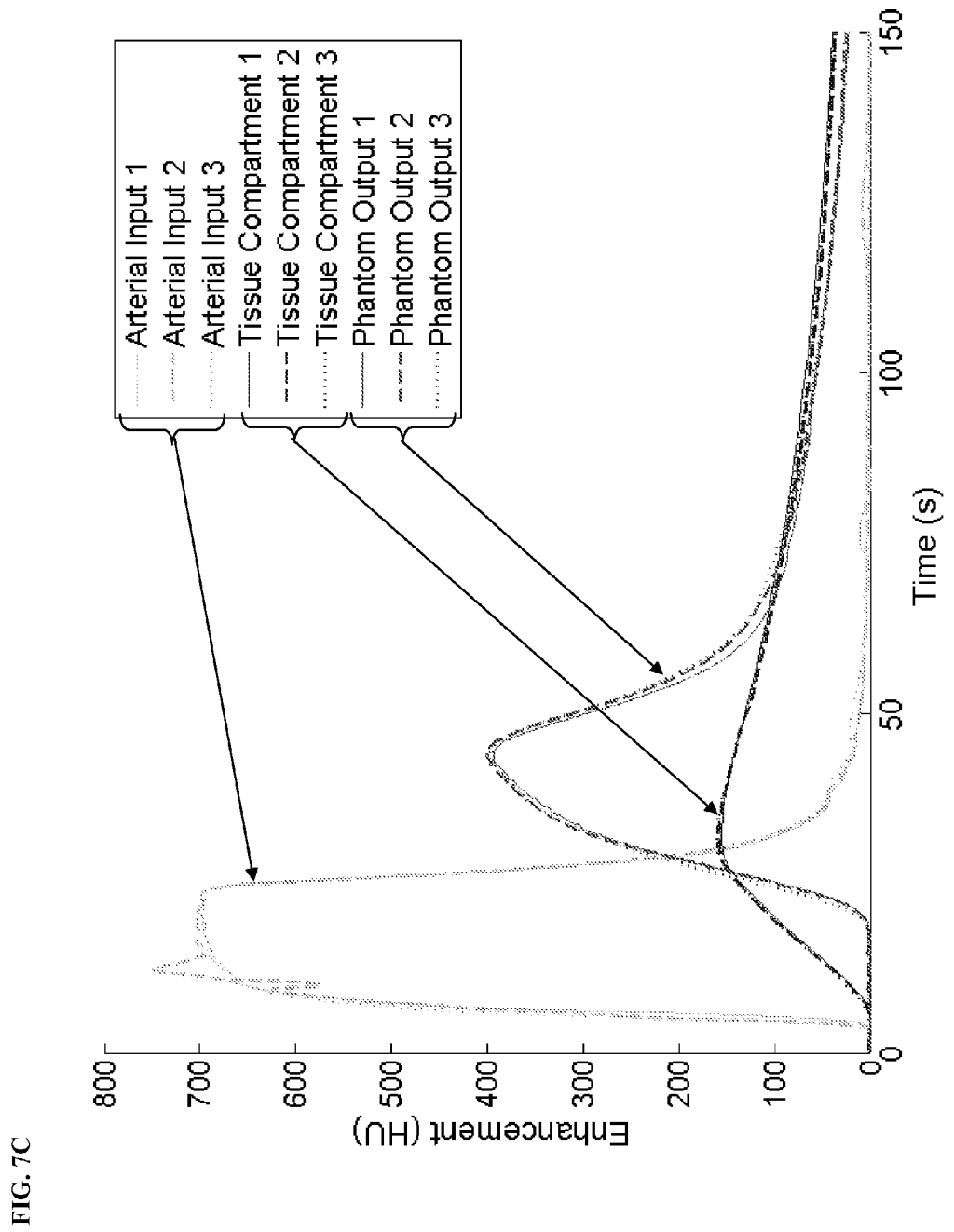
Figure 7D:
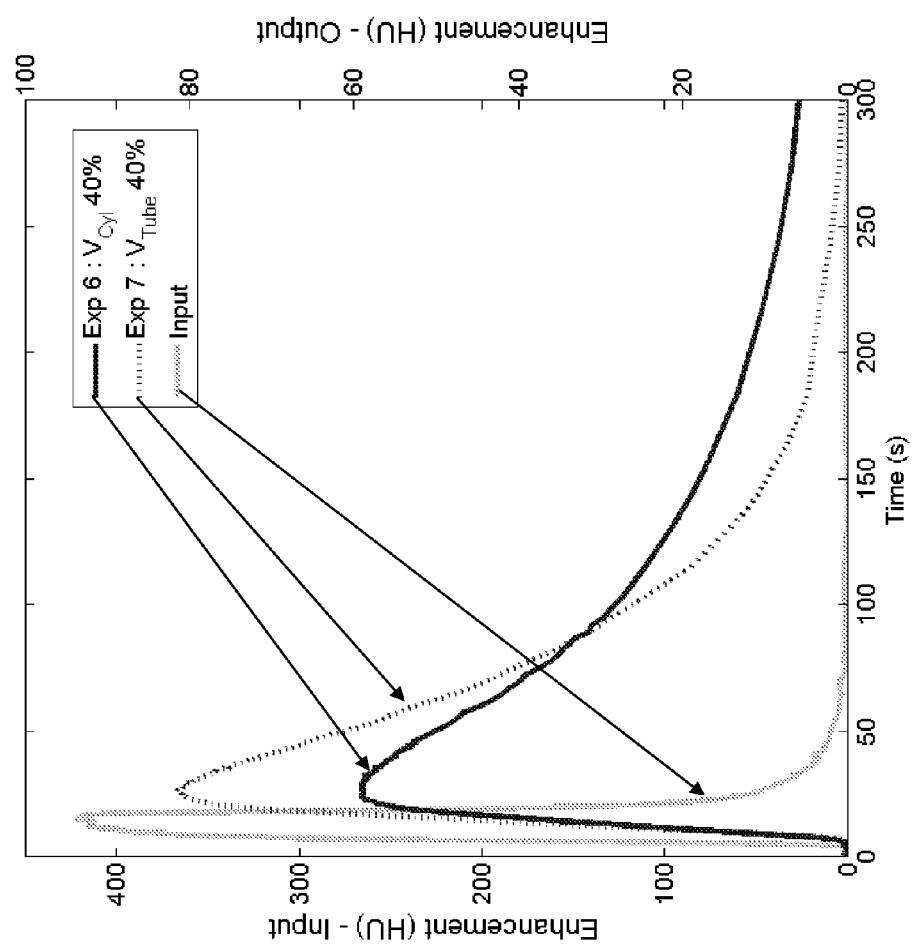

In a further study, a supplementary tube was added which collects the phantom outputs and passes back through the field of view of the scanner such that its intensity can also be measured (FIGS. 7A-7C).

Liver Study

Conventionally, analysis of liver perfusion is often done primarily by examining the arterial input to the liver ($C_a$) and its relation to the overall contrast level within the liver ($C_i$)[2].

In the brain it is typically the difference in uptake between healthy white or grey matter and tumor which is examined[11].

Figure 8A:
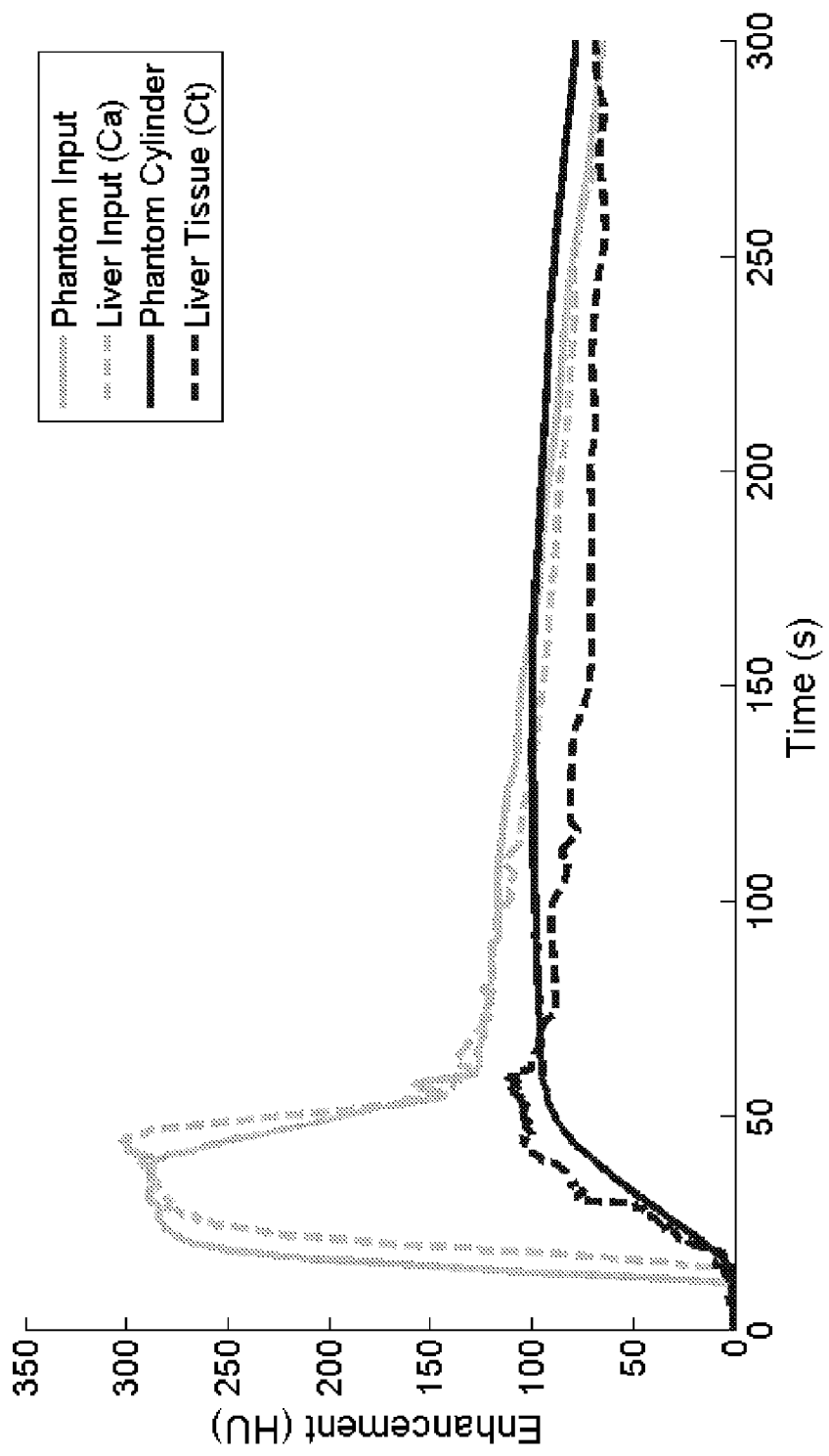
FIGS. 8A-8B shows comparisons of time intensity curves between an example phantom based on the liver and actual values.

FIG. 8A (Top hashed line) depicts an example of a perfusion CT time concentration curve of a human liver cancer patient. By simulating the arterial input from this patient with the injection pump and optimizing the flow rate and valve positions (e.g., using the phantom model described below) a similar time concentration curve may be created with the phantom (Solid Line FIG. 8A).

The perfusion parameters obtained from a standard Tofts model of both the clinical perfusion study and the phantom were analyzed in an effort to compare the results and are shown in Table 3 in FIG. 11.

Figure 8B:
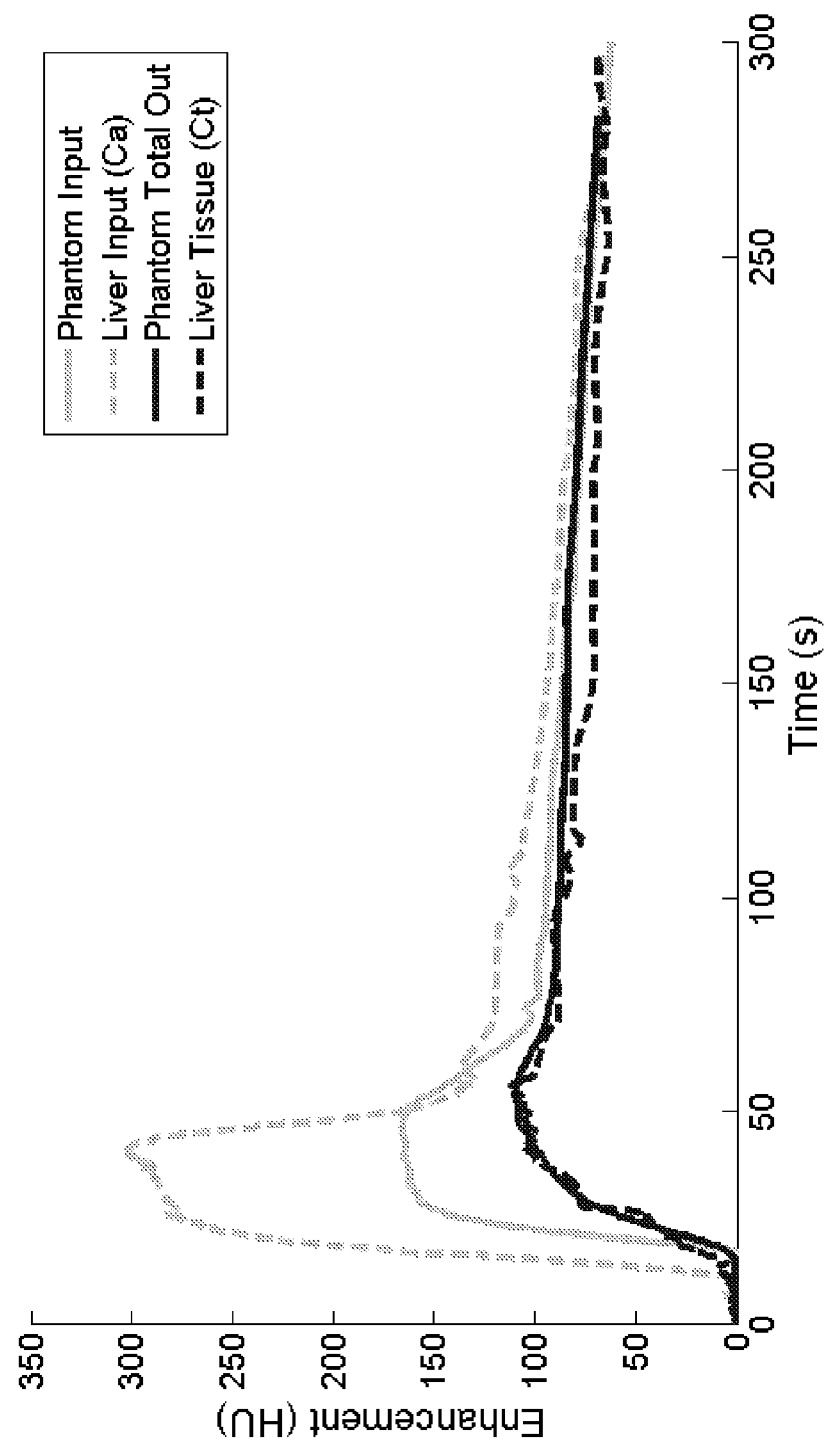

In this example, transfer constants $K_{trans}$ and $K_{ep}$ may be adjusted, such as using valve position, flow rate and/or injection function, and may include ranges both higher and lower than the clinical liver. In this example, because interstitial space is not modelled in this example phantom, it may be possible to currently generate either the exact arterial input function of a human liver or the tissue time concentration curve but not both tasks simultaneously. However, this may be addressed in other example phantoms, which may include some level of interstitial exchange. A second experiment was done to more closely mimic the liver tissue curve, in this example by applying a different input curve (FIG. 8B). The example results show that initial slopes of the clinical liver curve and the phantom generated curve are similar as are the curves themselves, even though the perfusion parameters are different from that of the clinical liver.

Since the perfusion parameters of the example phantom may be within an order of magnitude of those from a human organ, the phantom may be utilized to validate perfusion models of the liver, for example in the absence of motion or measurement uncertainties, under controlled and well defined conditions.

Brain Study

In addition to the liver, the example dynamic flow imaging phantom may be used to simulate the time intensity curves of a brain tumor. In this example study, a tumor time intensity curve was generated using the example phantom, given the arterial input function to the brain. In the brain the arterial input has an intensity of more than ten fold that of the tumor so, though the shape of the input curve was maintained, the intensity was reduced by a factor of 5.

Figure 9:
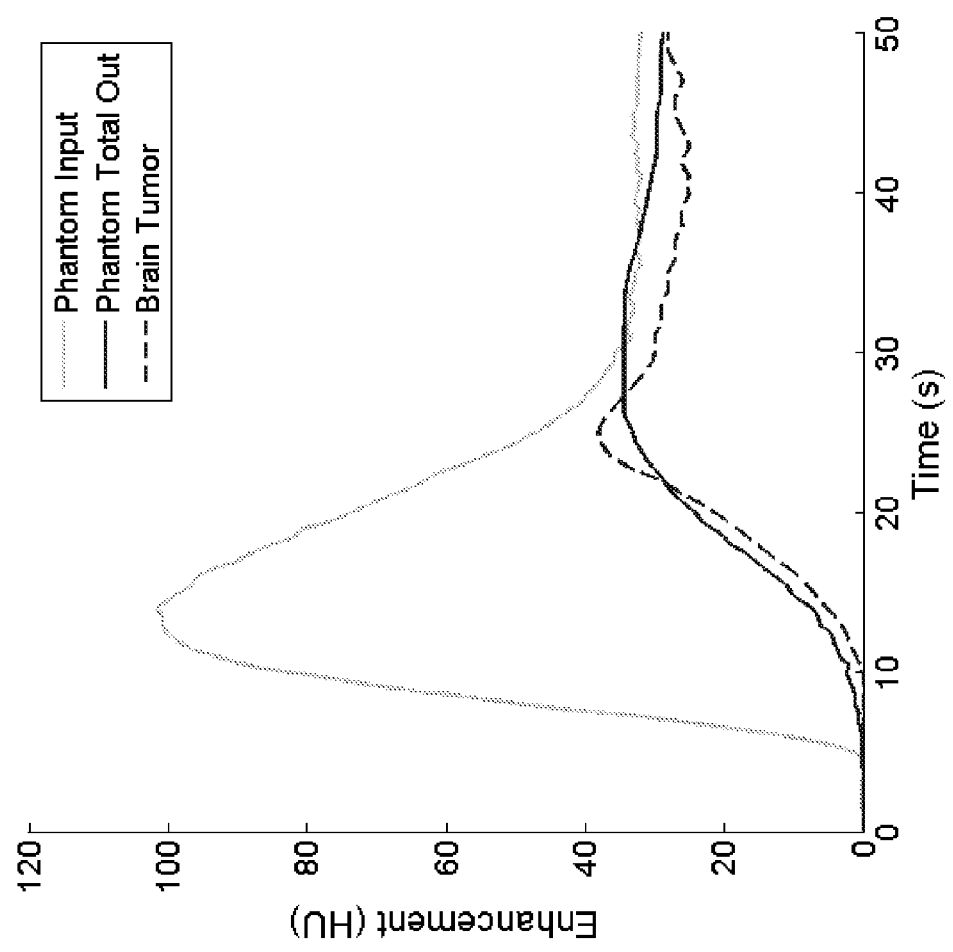
FIG. 9 shows comparisons of time intensity curves between an example phantom based on the brain and actual values.

FIG. 9 demonstrates the brain tumor generated curve as well as the input curve to the phantom used to create it. It may be possible to replicate the initial slope and peak height of the tumor very closely (see Table 4 in FIG. 11). In this example phantom, it may be difficult to mimic the tissue ½ retention time due to the rapidity of the clinical tumor reduction. However, the curves generated may be similar enough to be useful in validating brain perfusion kinetic models.

Other example phantoms may more closely replicate experiments in the brain with similarly fast pulses. For example, other phantoms may have decreased cylinder sizes and/or altered exchange mechanisms to decrease retention time.

Other example phantoms may include other representations of perfusion within the phantom. Other example clinical applications may include scanner QA and optimization of DCE CT scan protocols to limit patient dose. The phantom may be useful as a gold standard across multiple modalities including, for example, CT, PET and MRI, among others, for example with some suitable small alterations.

Phantom Variations

Although an example phantom has been described having a tube (as the first compartment) inside a cylinder (as the second compartment), other phantom configurations may be possible. For example, the first and second compartments may be separate from each other and communicate with each other via connections (e.g., external tubing). In some examples, the phantom may also be designed to be modular, such that the first and the second compartments may be individually changed. For example, where the first compartment is a tube, different tube diameters, lengths and/or materials may be used, and the tube may be configured to have different numbers of numbers and/or orifices.

In some examples, a plurality of phantoms may be used, such as in a parallel or a series configuration. For example, two two-compartment phantoms may be used in a series configuration to provide a four-compartment model.

In some examples, the phantom may be configured to sit inside the imaging area or outside the imaging area.

In some examples, the phantom may be configured to have a fluid exchange system different from the example orifices described above. For example the phantom may include a diffusion-based exchange mechanism (such as a fibre-base filtration or membrane system, which may be similar to a dialyser system, in addition to or in place of orifices) for communication of fluids between the first and second compartments. In some examples the phantom may include a microvascular fluid exchange system (e.g., in addition to or in place of orifices) for communication of fluids between the first and second compartments.

In some examples, the phantom may be configured to simulate the vasculature network of a physiological organ (e.g., a human liver or a human brain), for example by mimicking the shape, size, and/or permeability of the organ. Such an example phantom may include the use of a combination of orifices, diffusion membranes (e.g., a dialysis membrane) and/or microvascular exchange systems, which may mimic the different levels of fluid exchange found in an organ.

Model

Example studies of the example phantom described above were carried out to characterize the phantom with regards to various properties, including, for example, the range of the phantom, its reproducibility and the effectiveness of the output valves with regards to altering the shape of the output curve. In these examples, the parameters which were altered to produce various time concentration curves are the Perfusion Pump Flow Rate ($Q_{Pump}$) the Injection Pump Flow Rate ($Q_{Inject}$) the Injection Time ($t_{Inject}$) and the valve positions which control the ratio of the output flow rates ($V_{Cyl}:V_{Tube}$). The contrast concentration was diluted to 78.4 mg/ml or 150 mg/ml for each experiment.

Figure 12:
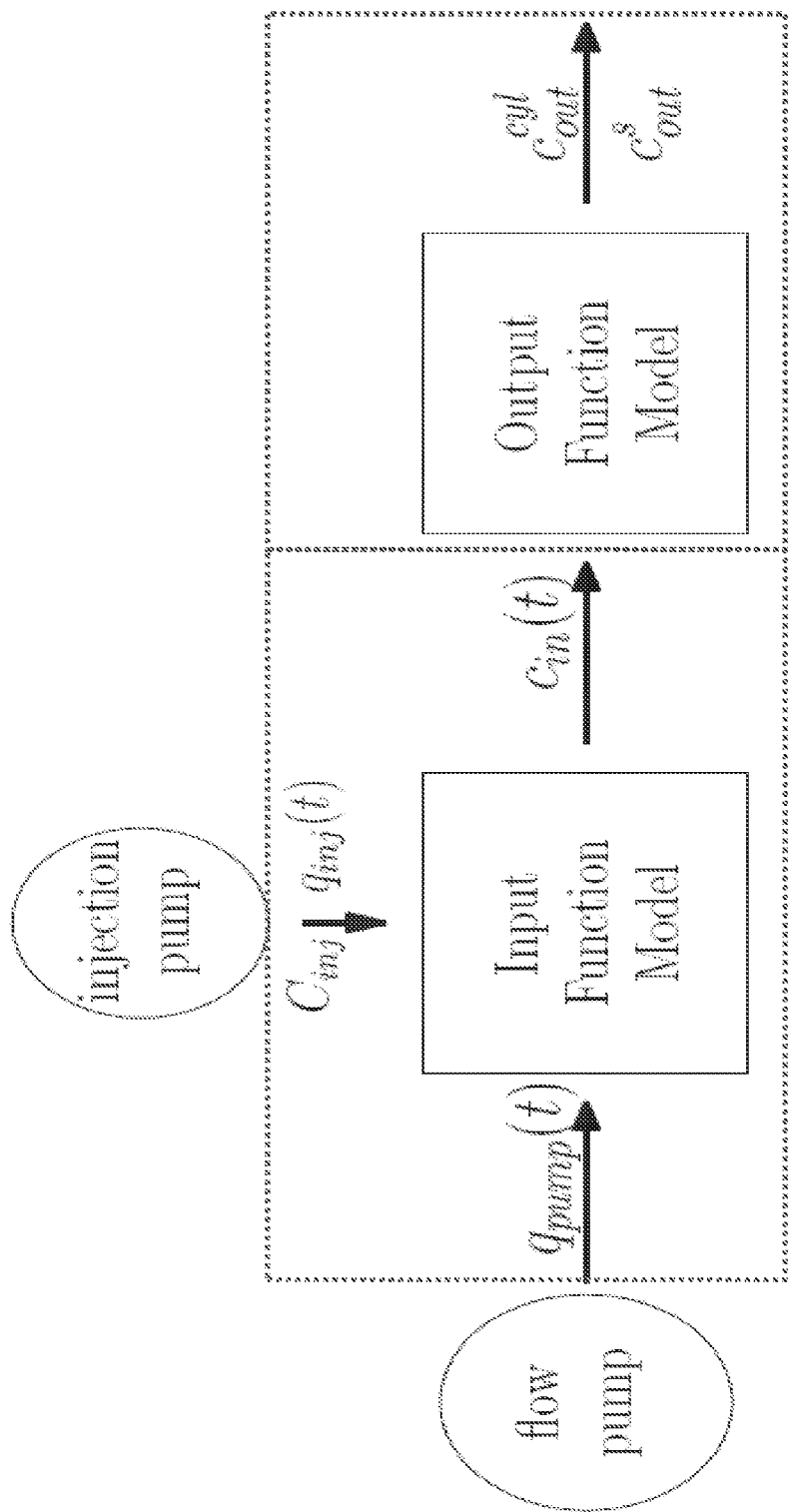
FIG. 12 is a schematic illustrating an example model for an example phantom.

In this example, the example phantom and its flow system were divided into two separate stages (FIG. 12). The first stage (left box) may be a model for the input function $c_{in}(t)$ into the example phantom given the injected concentration $C_{inj}$, the injection flow rate $q_{inj}(t)$ and the pump flow rate $q_{pump}(t)$. This model may be referred to as the input function model. The second stage (right box) may represent the exchange of mass which occurs within the example phantom for which a compartmental model can be created and may be referred to as the output function model.

Figure 13:
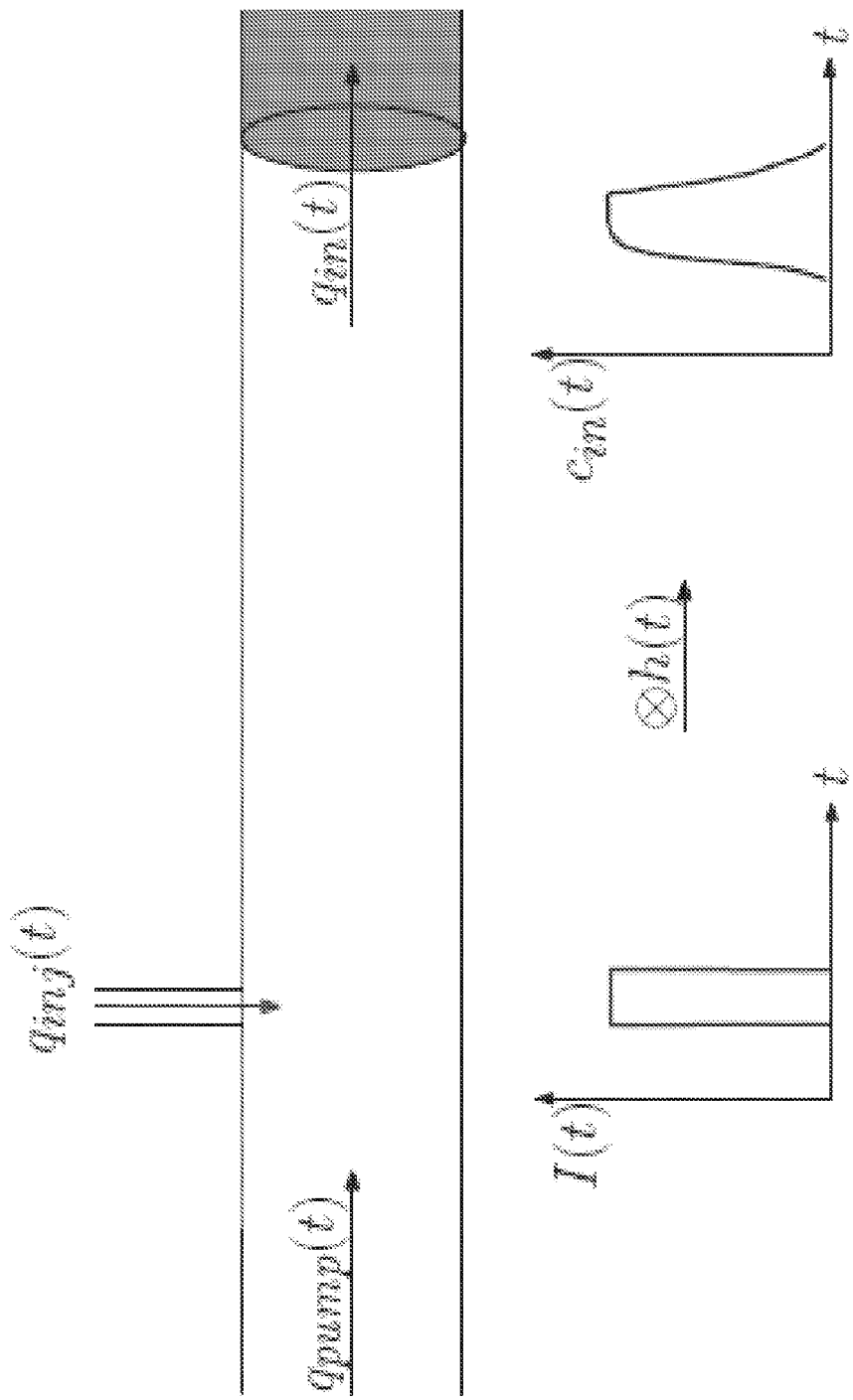
FIG. 13 schematically illustrates an example model for input to an example phantom.

The input function model (FIG. 13) may be a relatively simple model based on the deformation of I (the injection concentration, mg/ml) with a blurring function. In this example, I(t) is the concentration of contrast being injected into the system as a function of time based on the flow rates of the injection and flow pumps. The input function may be simply distorted to match characterization measurements using the equation:

$$c_{in}(t_k) = c_{in}(t_{k-1}) + \frac{\text{Max}(I(t)) - c_{in}(t_{k-1})}{\text{erf}(t_1)} \cdot \left[\text{erf}\left(\frac{t_1 + 2.2}{t_{up}} \cdot t - t_1\right) + \text{erf}(t_1)\right] \quad \text{Eq (1)}$$

The variable $t_{up}$ may represent the time for the error function to reach the plateau and $t_1$ determines the initial position of the error function. These two parameters may be fit to the shape of the input curve from the characterization measurements and the same values may be then used for other model predictions.

Figure 14:
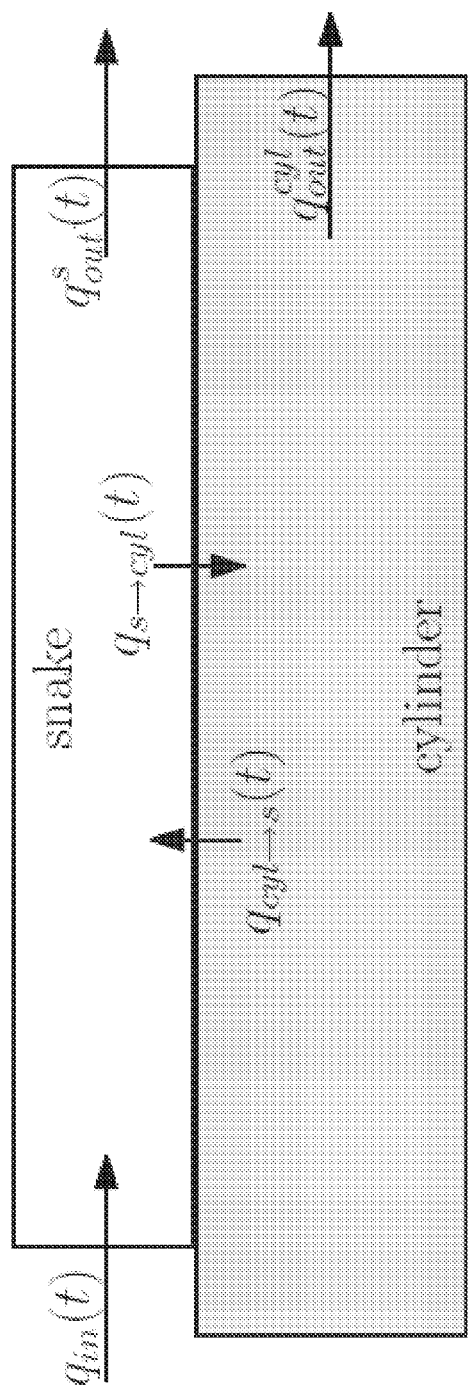
FIG. 14 schematically illustrates flow rates considered in an example model.

This example model may be varied, for example by simulating a delta function with the injection pump and analyzing its conformation along the tube at different flow rates. This simple wave form h(t) can then be convolved with I(t) to generate $c_{in}(t)$ The output function model may be based on a two-compartment model in which mass is exchanged between the two compartments in discrete time steps (for example as shown in FIG. 14). In order to derive expressions for the output flow rate at the cylinder $q_{cyl}^{out}(t)$ and the output flow rate at the end of the tube $q_{tube}^{out}(t)$, a fundamental parameter, R, was defined as the ratio of the input flow rate $q_{in}$ that leaves the through the cylinder:

$$R = \frac{q_{out}^{cyl}(t)}{q_{in}(t)} \quad \text{Eq (2)}$$

Based on characterization of the output ratio based on valve position (e.g., as described in the example studies above), the value of R may be known. It may be assumed that the effect of the N holes of the tube may be described as an aggregate effect, and thus it may be possible to determine the value of r, the fraction of flow at each hole that leaves through the hole rather than continue along the tube. However, if there is flow from the cylinder back into the tube ($r_{ret}$) it may also be accounted for such that the r value for an individual compartment s represented by:

$$r = \frac{(1 - r_{ret}) \cdot q_{s \to cyl}^{i}(t)}{(1 - r_{ret}) \cdot q_{s \to cyl}^{i}(t) + q_{out}^{i}(t)} = \frac{(1 - r_{ret}) \cdot q_{s \to cyl}^{i}(t)}{q_{out}^{i-1}(t)} \quad \text{Eq (3)}$$

where $$r = 1 - (1 - R)^{\frac{1}{N}} \quad \text{Eq (4)}$$

The value of $r_{ret}$ can be obtained from the initial DCE-CT measurements, for example by observing what value of $r_{ret}$ produced the best fit of the contrast input and tube output time concentration curves.

In order to correctly predict the temporal behavior of $q_{tube}^{out}(t)$ from the input flow rate $q_{in}(t)$, it may be useful to employ a model that predicts both the temporal and the spatial behavior of the liquid flow through the tube. A traditional compartment model may not take into account the spatial distribution of a concentration.

An extension to the traditional compartment model may be made, to obtain a 'spatio temporal' version of such a model that may allow computation of the time-concentration curves of the tube at any given tube location. For this purpose, 'mobile' compartments may be introduced that contain a known amount of liquid at a given time. These compartments may be 'created' at the entrance of the tube which is denoted by the location x=0. The initial volume of such a compartment may be determined by the flow rate $q_{in}(x=0, t)$ and the finite time interval $\Delta t$ such that:

$$\Delta V_k(0, t_k) = q(0, t_k) \cdot \Delta t \quad \text{Eq (5)}$$

Figure 15:
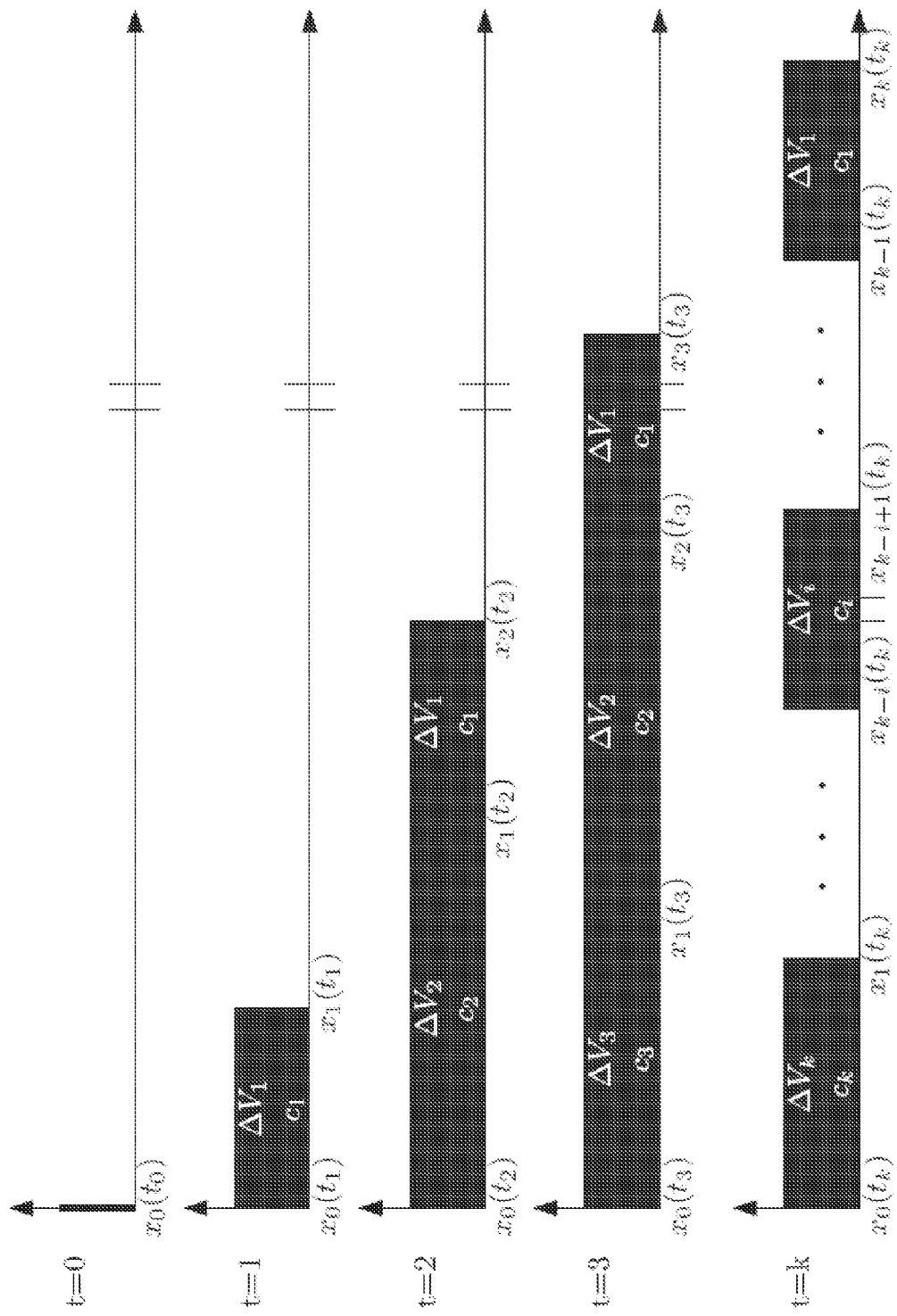
FIG. 15 illustrates the spatio-temporal nature of an example model.

FIG. 15 shows an example of these compartments, defined by their borders which are labeled with $x_i$ and depend on time $x_i(t_k)$. The position of $x_i(t)$ can then be calculated recursively from the positions of the previous time step:

$$x_i(t_k) = x_{i-1}(t_{k-1}) + \frac{1}{A}[q(x_{i-1}(t_{k-1}), t_{k-1}) \cdot \Delta t] \quad \text{Eq (6)}$$

After time step k, and just before the (k+1)th time step, the flow rate at each compartment boundary may be given by:

$$q(x_i(t_k), t_k) = q_{in}(t_k) \cdot (1 - r)^{\left\lfloor \frac{x_i(t_k)}{\frac{L}{N+1}} \right\rfloor} \quad \text{Eq (7)}$$

The exponent is an integer that counts the number of holes that were traversed by the boundary $x_i(t_k)$. The bracket denotes the floor function.

During each time step ($t_k$) liquid may leave and reenter the tube through the holes. This may result in a change of concentration for those volumes $\Delta V_i$ whose left and right boundaries encompass a hole. But for all the other compartments which do not encompass a hole, the concentration is unchanged during this time step.

The mass $\Delta m_{out}$, which leaves the volume $\Delta V_i(t_k)$ into the cylinder, can be calculated in the following way, using the definition of r:

$$\Delta m_{out}(t_k) = c'_i(t_k) \cdot q(x_{k-i}(t_k), t_k) \cdot \Delta t \cdot \frac{r}{1 - r_{ret}} \quad \text{Eq (8)}$$

$$= c_i(t_{k-1}) \cdot q(x_{k-i}(t_k), t_k) \cdot \Delta t \cdot \frac{r}{1 - r_{ret}}$$

For $\Delta m_{in}$, similarly:

$$\Delta m_{in}(t_k) = c_{cyl}(t_{k-1}) \cdot q(x_{k-i}(t_k), t_k) \cdot \Delta t \cdot r_{ret} \cdot \frac{r}{1 - r_{ret}} \quad \text{Eq (9)}$$

Starting from the known concentration before the exchange, $c'_i(t_k)$, the new concentration $c_i(t_k)$ may be calculated as follows:

$$c_i(t_k) = \frac{c'_i(t_k) \cdot \Delta V_i(t_k) - (c'_i(t_k) - c_{cyl}(t_{k-1}) \cdot r_{ret}) \cdot q(x_{k-1}(t_k), t_k) \cdot \Delta t \cdot \frac{r}{1 - r_{ret}}}{\Delta V_i(t_k) - q(x_{k-1}(t_k), t_k) \cdot \Delta t \cdot r} \quad \text{Eq (10)}$$

Similarly the concentration of the cylinder can be calculated by determining the cumulative mass into the cylinder from the holes and subtracting what leaves.

$$c_{cyl}(t_k) = c_{cyl}(t_{k-1}) + \frac{\left(\sum_{i=1}^{N} \Delta m_{out}^i(t_k) - \Delta m_{in}^i(t_k)\right) - (q_{in}(t_k) - q_{out}^{s,N}(t_k)) \cdot \Delta t \cdot c_{cyl}(t_{k-1})}{V_{cyl}} \quad \text{Eq (11)}$$

By calculating the values of $x_i(t)$, $q(x, t)$ $c_i(t)$ and $c_{cyl}(t)$ it may be possible to keep track of the concentration of the liquid in any tube compartment and in the cylinder at any give time and position. This modeled data can then be compared against the results of an actual imaging scan (e.g., DCE-CT scan) to compare the results.

The example model may be able to relatively quickly generate a set of time concentration curves given the experimental parameters. Thus, the example model may be applied in an optimization strategy to determine experimental parameters in order to generate a desired time concentration curve or set of curves.

For example, a software program may import a target input and/or output time concentration curve from clinical or QA data. The range of the experimental parameters to search may be adjusted (e.g., manually) (e.g., $Q_{pump}$>2 & <5, R value between 0.3 & 0.8 etc). An optimization may be performed in which the experimental parameters may be varied (e.g., based on the example model described above) and the resulting predicted time concentration curves may be compared to the target functions, which may help to minimize or reduce the sum of squared errors between the target and predictions.

For producing an appropriate output curve, both the cylinder and total output flow time concentration functions may be compared to the target output and whichever has the lower error may be selected. This may increase the range of potential target curves the example phantom can simulate as the two flows typically have different characteristics.

Once the optimal solution is identified it may be displayed graphically for the user and the necessary experimental parameters may be provided such that they can be applied to the phantom to generate the desired curve.

Example experiments on the phantom, for example as described above, may allow for adjustment of various model parameters, such as the $R_{ret}$ parameter which represents the backflow from the cylinder into the tube which is typically difficult or impossible to measure with flow alone. The example experiments may also allow for a preliminary model of the blurring that occurs to the step function input as it mixes along the input tubing. This function may be optimized for the preliminary data set and may then be applied to the subsequent experiments utilizing those values. Other example experiments may model the blur function in other ways, for example by creating a series of delta functions with the injection pump at various flow rates which can be directly convolved with the input injection function.

Other step function injection experiments may test different experimental parameters than those described above. For example, an example experiment may use a simple step function 20 seconds in length and a total scan time of 300 seconds. An experiment of this nature may be useful for doing DCE-CT quality assurance on a CT scanner with the example phantom and as such it may be desirable that the model relatively accurately predict the result and that the results are relatively reproducible. In the example studies described above, the reproducibility of the phantom was found to be relatively consistent and the example model predictions were relatively reliable.

Figure 16:
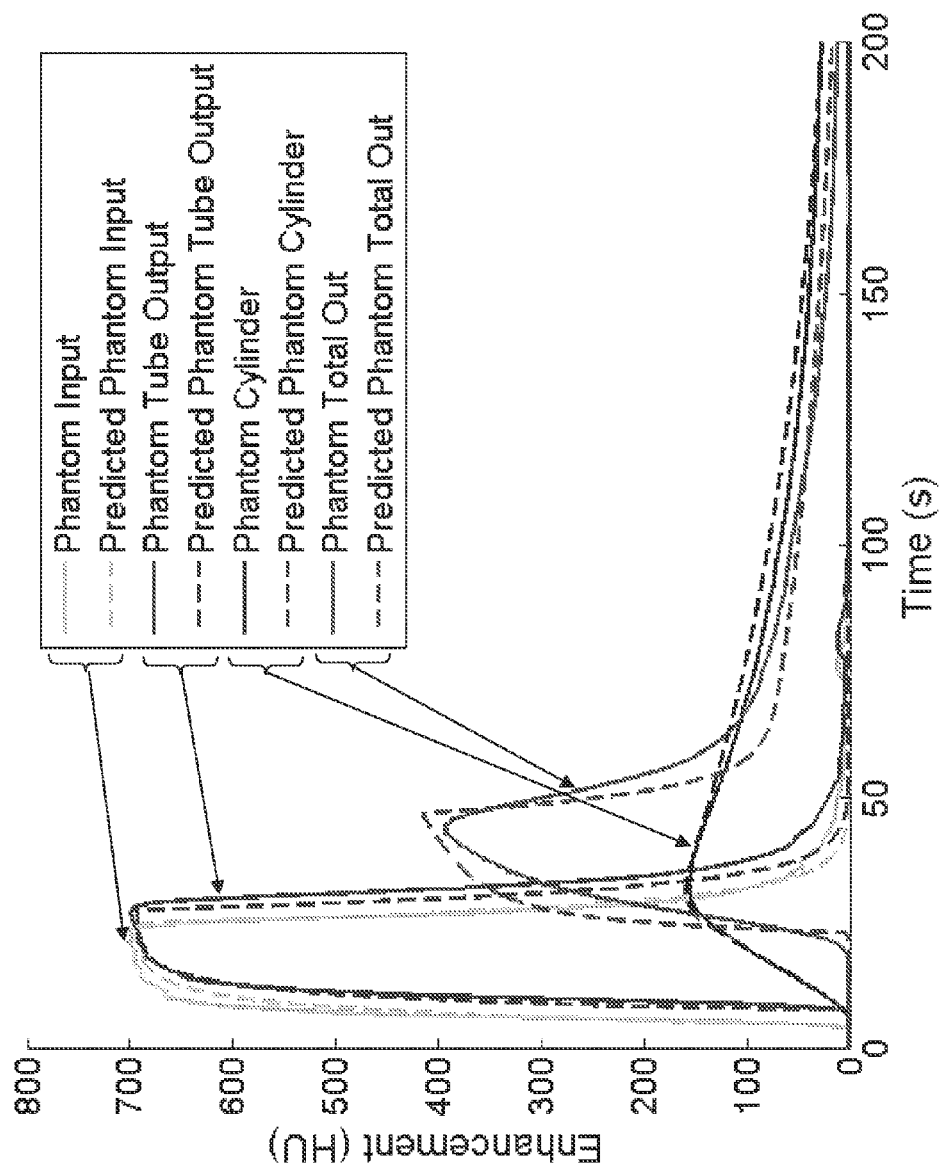
FIG. 16 is a plot comparing results from an example model with results from an example phantom.

FIG. 16 illustrates example curves comparing results from the example model to experimental results from the example phantom. The hashed line represents the model predictions for the step function pulse and whereas the experimental results are represented by solid lines, the results were also analyzed numerically and are listed in Table 5. Of the 4 input or output functions only the total output prediction (magenta line) shows any substantial deviation from the prediction ($R^2$=0.92±0.04). This may be due to a blurring which occurs between the two phantom outputs and its eventual return to the image field as a combined flow. The area under the curve of both functions is in good agreement ($\Delta$ $AUC_{200}$=2.3±1.5%). All other curves had goodness of fits of 0.96 or better.

The total injected mass was also calculated and compared to both the experimental result as well as the actual mass. The actual mass is known (3000 mg) and the experimental results show values of 3129±6.9 whereas the model predicts an injected mass of 3012.8 mg. The error in the injected mass in the model may be a result of the imperfect blur function being applied to the input function, whereas the error in the experimental result may be the result of a combination of partial voluming in the tube and inaccurate mixing of the contrast in the injection syringe.

With an example phantom having a relatively simple two compartment model, it may not always be possible to create both a representative input and output time concentration curve, however each may be represented individually. The example model may predict this behaviour and may allow for the determination of the range of the phantom without the need to perform a wide range of DCE-CT experiments.

Using clinical perfusion data from a liver perfusion CT two subsequent experiments were designed for the phantom: an experiment modeling the arterial input function of the liver as well as one modeling the liver tissue time concentration curve. In both cases the optimization was performed such that the model predicted a relatively close representation of either the input or the output and then the corresponding output/input was fit as well as possible provided the range of the phantom. The model then produced the experimental parameters necessary in order to perform the experiments.

Figure 17A:
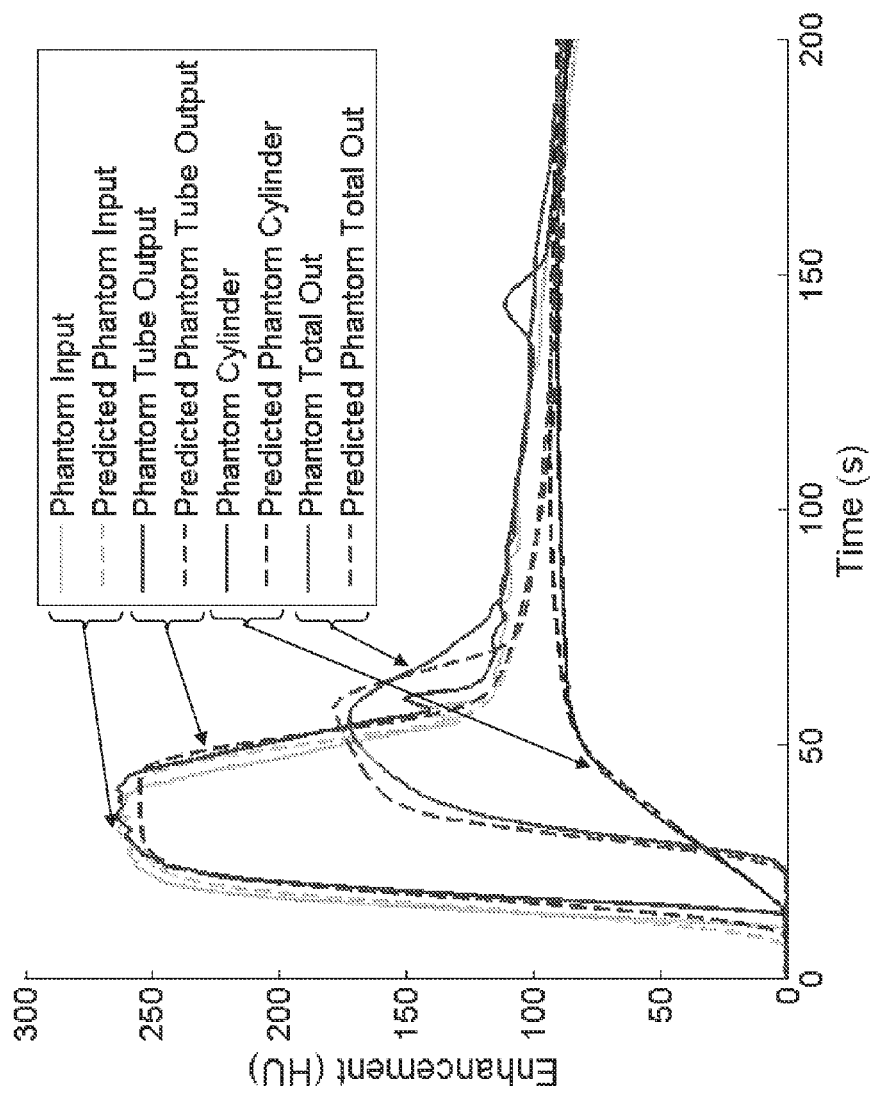
FIGS. 17A and 17B are plots comparing results from an example model with results from an example phantom.
Figure 17B:
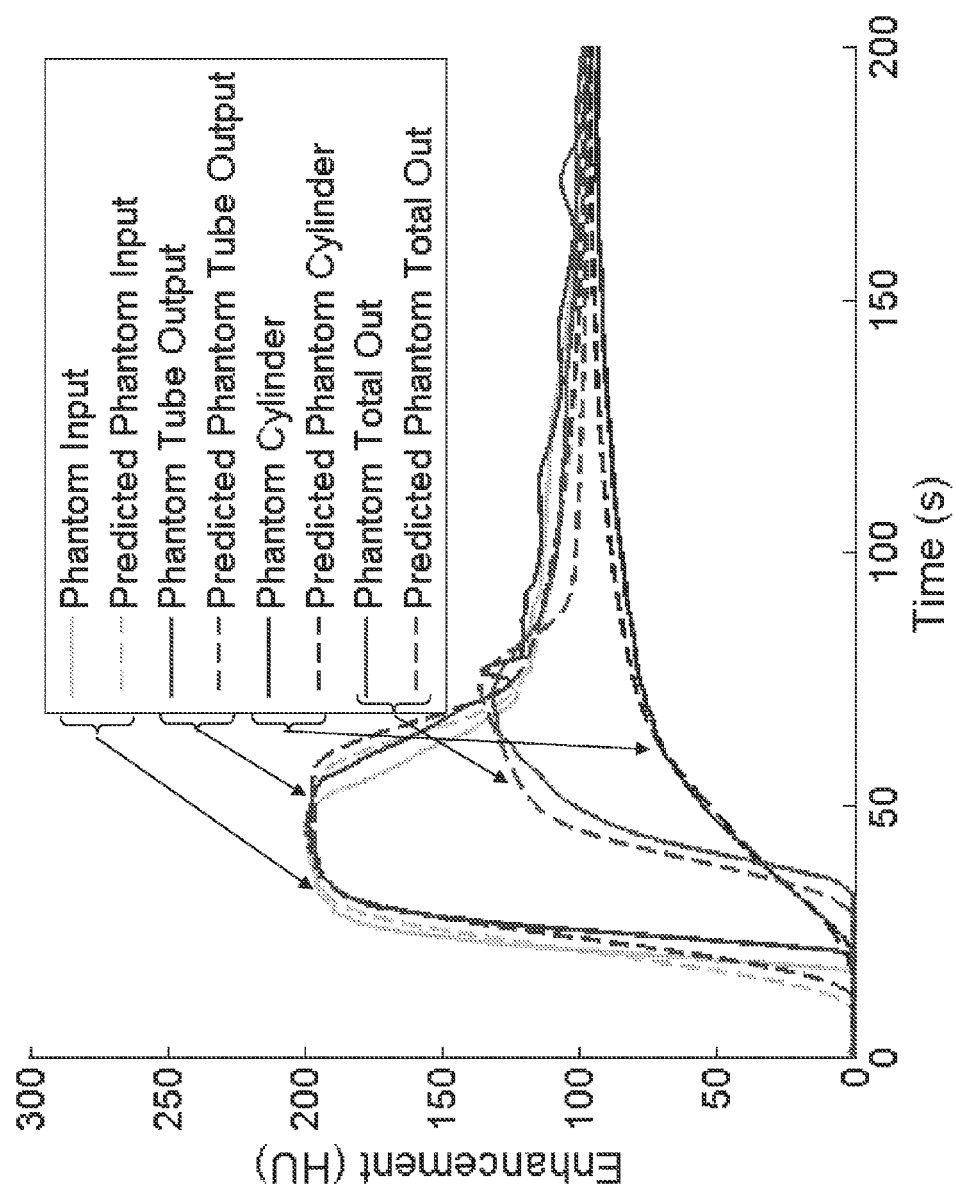

As was the case with the simple step function experiment, the model predictions were once again relatively accurate when compared with the experimental results (FIGS. 17A and 17B & Table 5). All 4 curves for each experiment displayed a goodness of fit, as assessed by $R^2$, of 0.94 or better. The projected peak heights were also modeled with an error of less than 4% for each of the 4 different input/output functions. A comparison of the injected mass to the predictions provided a final confirmation as to the accuracy of the model predictions. The error for the arterial function simulation perfusion curve was 1.16±0.85% whereas the error in the liver tissue time concentration curve was accurate to within 4.09±1.02%.

Study of Example Phantom Using a Dialyser

In an example study, the phantom may be based on a haemodialyser. A haemodialyser may refer to a device designed to filter out harmful substances in the blood of patients with a kidney disease. The dialyser may utilize ultrafiltration (i.e., movement of molecules due to hydrostatic pressure force) and diffusion (i.e., movement of molecules due to osmotic pressure force) similar to how capillaries exchange solutes. In an example dialyser, blood may flow through a central compartment made of multiple micro vessels, such as 10000 vessels, each with a 200 μm diameter. This central compartment may be surrounded by a space where dialysate buffers may flow to filter out any solutes smaller than the size of dialyser's pores.

The example phantom may take the advantage of the dialyser's capillary exchange system concept. The dialyser may follow a restricted diffusion model of capillary permeability, where relatively uniform pores (e.g., with diameters between 6 to 9 nm) may account for the observed rates of passage of water and lipid soluble molecules in capillaries[65]. As such, an example contrast diffusion phantom was developed using a dialyser, for validation of perfusion studies. A schematic drawing and a picture of an experimental set-up using such an example phantom is shown in FIG. 19 and FIG. 20, respectively.

Figure 19:
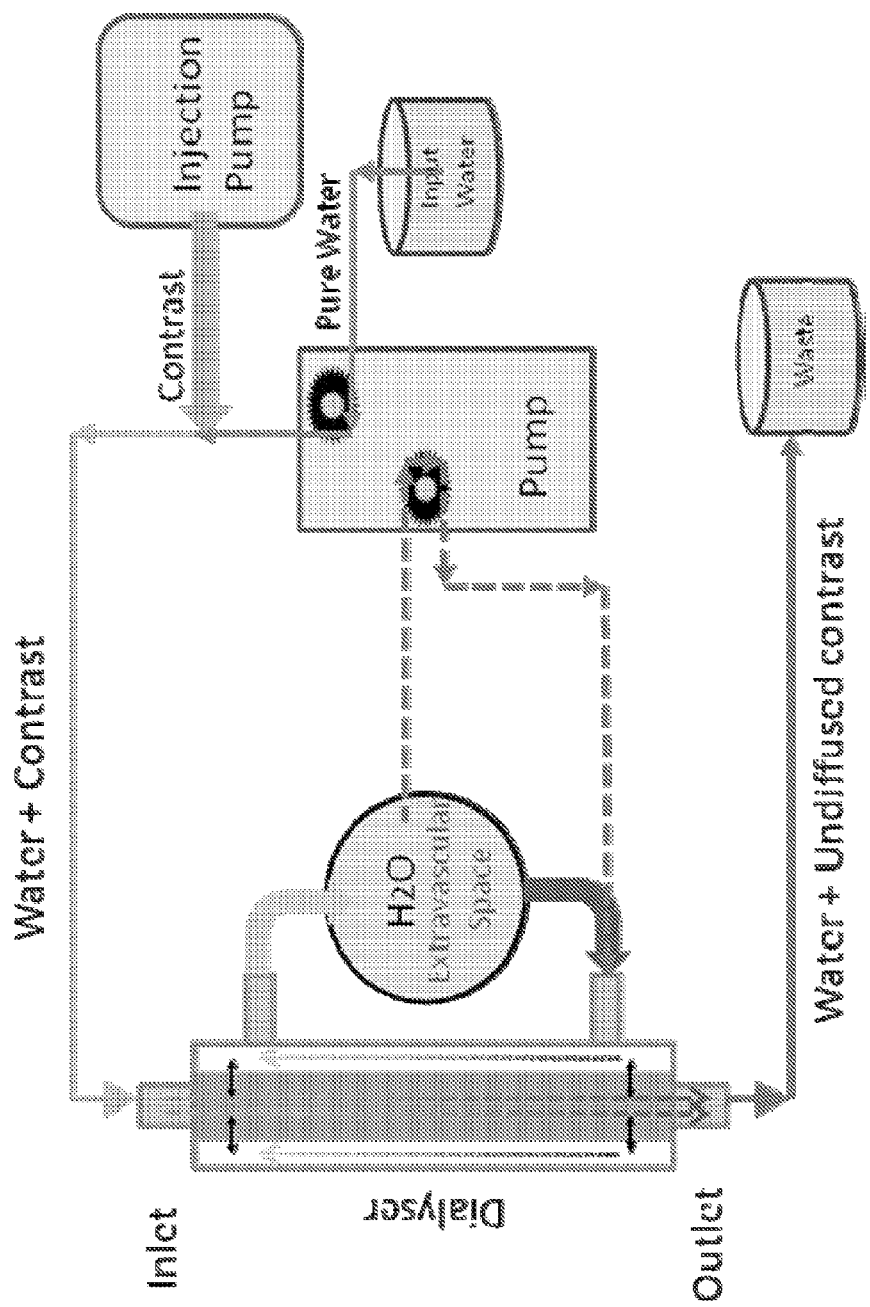
FIG. 19 is a schematic showing an example setup using an example phantom using a dialyser.
Figure 20:
FIG. 20 is an image showing the example setup of FIG. 19.

As illustrated in FIG. 19, in this example study, pure water may be pumped (e.g., by a roller pump) into the inlet of the dialyser. On its way to the dialyser, this pure water may be mixed with a contrast agent (e.g., via an injection pump, which in this example may injects 30 mL of contrast at a rate of 1 mL/sec). This mixture may then travel through the dialyser where a constant exchange occurs between the dialyser (representing the blood vessel) and the water reservoir (representing the extravascular space). The water in the reservoir may be recycled throughout the experiment. Non-diffused contrast mixture may then come out of the outlet into the waste bucket.

Figure 21:
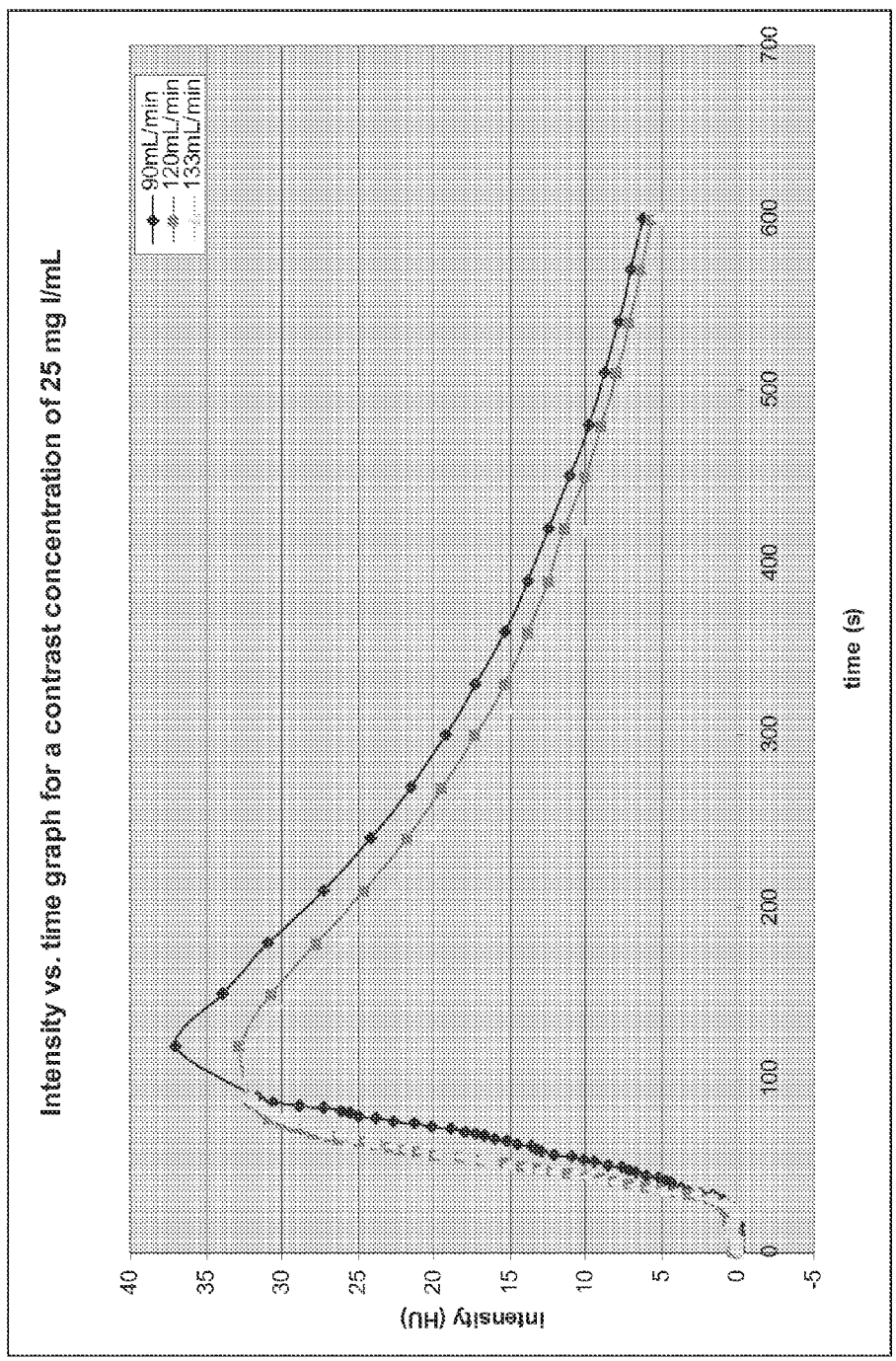
FIGS. 21 and 22 are charts obtained from the example setup of FIG. 19, illustrating the effects of flow rate and concentration of contrast on extravascular enhancement curves.
Figure 22:
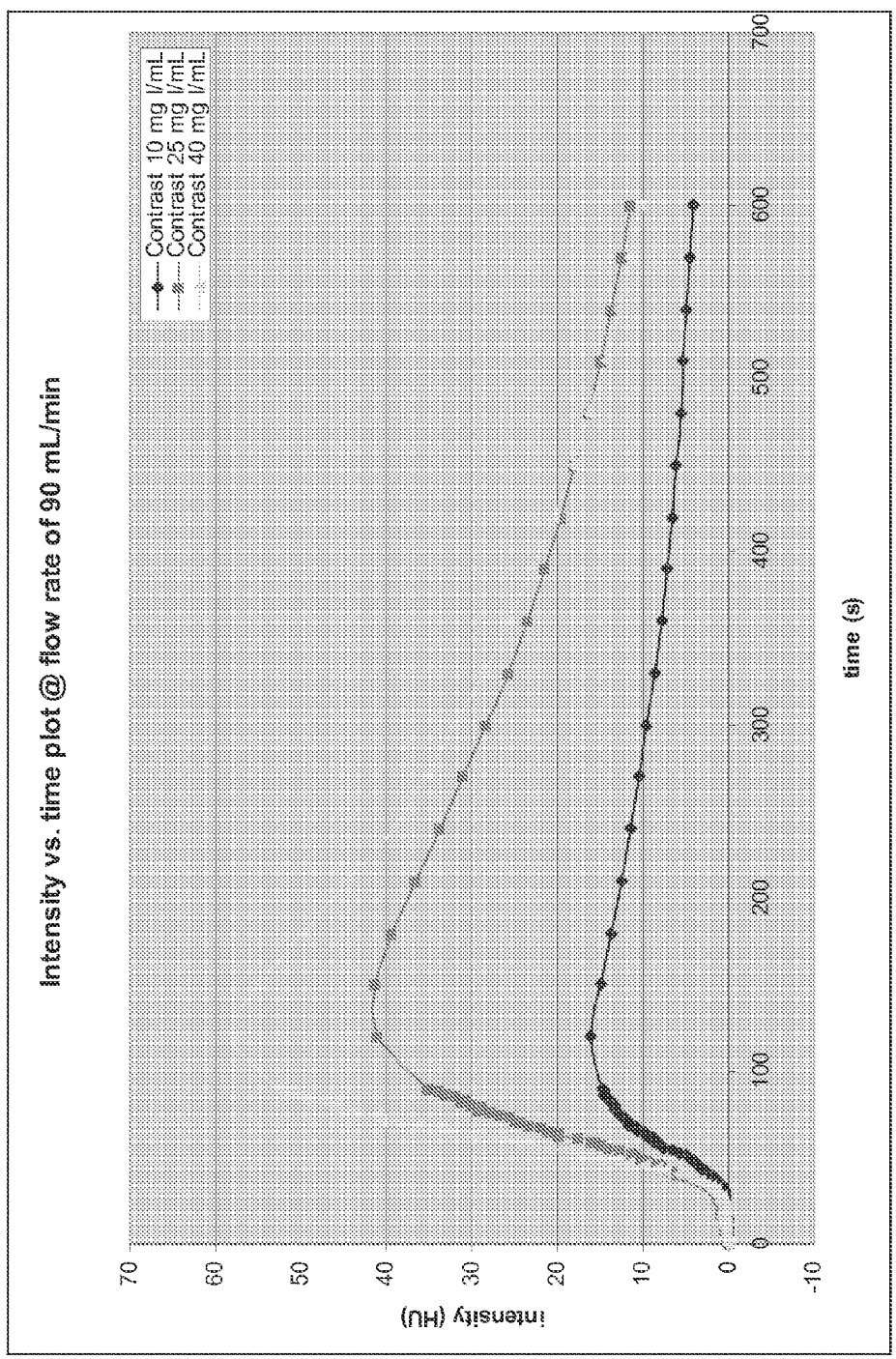

Results from this example study confirmed that the example phantom does indeed show diffusion of contrast agent from the dialyser to the "extravascular space" and the subsequent backflow of the contrast into the dialyser, as illustrated in FIGS. 21 and 22. FIG. 21 is a chart illustrating the impact of flow rate on extravascular enhancement curves. FIG. 22 is a chart illustrating the impact of concentration of contrast on extravascular enhancement curves.

In this example study, the diffusion rates were found to be only slightly affected in an experiment with different flow rates and a constant concentration of contrast, but changed considerably in an experiment with different concentrations of contrast and a constant flow rate. A kinetic model (such as the Adiabatic Tissue Homogeneity model) may be developed to fit the perfusion curves of the phantom and to use an example of this approach to further validate perfusion studies.

Applications

The disclosed dynamic flow imaging phantom may be capable of generating physiologically relevant time concentration curves as a result of the spatio temporal model. The disclosed model may allow for not only the prediction of the resulting time concentration curve given a set of experimental parameters but may also allow for the optimization of experimental parameters to generate a desired curve. The model may be useful for predicting the results across a range of situations, for example ranging from relatively simple step functions to relatively complex input wave forms.

Variations to the input function model may allow it to more accurately predict the blurring effect at different flow rates for any bolus injection. Similarly the phantom may be varied to address the blurring that occurs between the phantom exit and when it is imaged as the combined flow.

The perfusion CT data of other organs, such as the liver and brain, among others, may be fit and produced using the disclosed phantom and model.

The phantom and model may also be useful for various imaging modalities, including, for example, CT, PET and MRI.

The phantom and model may be useful for validation of kinetic models of perfusion as well as quality assurance and validation of imaging modalities.

The disclosed phantom and model may be used for validation of contrast enhancement measurements. The disclosed phantom and model may also be used as predictive or kinetic models. Use of the disclosed phantom and model may help to improve imaging techniques (e.g., may help to determine lower dosages). When used for calibration purposes, the disclosed phantom and model may allow for quantitative diagnoses and treatments.

The disclosed phantom and model may be used as a complement to a microvascular perfusion model. For example, the disclosed phantom may mimic macro behaviour of organs while a microvascular model may mimic micro behaviour of a tumour within the organs. This may be achieved, for example, by including a microvascular perfusion model in communication with the first and/or the second compartment of the disclosed phantom.

The embodiments of the present disclosure described above are intended to be examples only. Alterations, modifications and variations to the disclosure may be made without departing from the intended scope of the present disclosure. In particular, selected features from one or more of the above-described embodiments may be combined to create alternative embodiments not explicitly described. All values and sub-ranges within disclosed ranges are also disclosed. The subject matter described herein intends to cover and embrace all suitable changes in technology. All references mentioned are hereby incorporated by reference in their entirety.

REFERENCES

1. Huda W, Scalzetti E M, Levin G 2000 Technique factors and image quality as functions of patient weight at abdominal CT *Radiology* 217 430-435.
2. Miles K A. Perfusion CT for the assessment of tumour vascularity: which protocol? *Br J Radiol* 2003; 76 Spec No 1:S36-42.
3. Axel L. Cerebral blood flow determination by rapid-sequence computed tomography: theoretical analysis. *Radiology* 1980; 137:679-686.
4. Blomley M J, Coulden R, Bufkin C, et al. Contrast bolus dynamic computed tomography for the measurement of solid organ perfusion. *Invest Radiol* 1993; 28 Suppl 5:S72-77; discussion S78.
5. Blomley M J, Dawson P. Bolus dynamics: theoretical and experimental aspects. *Br J Radiol* 1997; 70:351-359.
6. Miles K A. Measurement of tissue perfusion by dynamic computed tomography. *Br J Radiol* 1991; 64:409-412.
7. St Lawrence K S, Lee T Y. An adiabatic approximation to the tissue homogeneity model for water exchange in the brain: I. Theoretical derivation. *J Cereb Blood Flow Metab* 1998; 18:1365-1377.
8. Cenic A, Nabavi D G, Craen R A, et al. Dynamic CT measurement of cerebral blood flow: a validation study. *AJNR Am J Neuroradiol* 1999; 20:63-73.
9. Cenic A, Nabavi D G, Craen R A, et al. A CT method to measure hemodynamics in brain tumors: validation and application of cerebral blood flow maps. *JNR Am J Neuroradiol* 2000; 21:462-470.
10. Koh T S, Zeman V, Darko J, et al. The inclusion of capillary distribution in the adiabatic tissue homogeneity model of blood flow. Phys Med Biol 2001; 46:1519-1538.
11. Koh T S, Markus Tan C K, Dennis Cheong L H, and Tchoyoson Lim C C. 2006 Cerebral perfusion mapping using a robust and efficient method for deconvolution analysis of dynamic contrast-enhanced images. *NeuroImage* 32 643-653.
12. Blomley M J, Coulden R, Bufkin C, et al. Contrast bolus dynamic computed tomography for the measurement of solid organ perfusion. *Invest Radiol* 1993; 28 Suppl 5:S72-77; discussion S78.
13. Blomley M J, Dawson P. Bolus dynamics: theoretical and experimental aspects. *Br J Radiol* 1997; 70:351-359.
14. Miles K A. Measurement of tissue perfusion by dynamic computed tomography. *Br J Radiol* 1991; 64:409-412.
15. Koh T S, Zeman V, Darko J, et al. The inclusion of capillary distribution in the adiabatic tissue homogeneity model of blood flow. *Phys Med Biol* 2001; 46:1519-1538.

16. St Lawrence K S, Lee T Y. An adiabatic approximation to the tissue homogeneity model for water exchange in the brain: I. Theoretical derivation. *J Cereb Blood Flow Metab* 1998; 18:1365-1377.
17. Cenic A, Nabavi D G, Craen R A, et al. Dynamic CT measurement of cerebral blood flow: a validation study. *AJNR Am J Neuroradiol* 1999; 20:63-73.
18. Cenic A, Nabavi D G, Craen R A, et al. A CT method to measure hemodynamics in brain tumors: validation and application of cerebral blood flow maps. *AJNR Am J Neuroradiol* 2000; 21:462-470.
19. Folkman J. What is the evidence that tumors are angiogenesis dependent? *J Natl Cancer Inst* 1990; 82:4-6.
20. Rajendran J G, Krohn K A. Imaging hypoxia and angiogenesis in tumors. *Radiol Clin North Am* 2005; 43:169-187.
21. Jain R K. Barriers to drug delivery in solid tumors. *Sci Am* 1994; 271:58-65.
22. Jain R K. Determinants of tumor blood flow: a review. *Cancer Res* 1988; 48:2641-2658.
23. Videtic G M, Belderbos J S, Spring Kong F M, et al. Report from the International Atomic Energy Agency (IAEA) consultants' meeting on elective nodal irradiation in lung cancer: small-cell lung cancer (SCLC). *Int J Radiat Oncol Biol Phys* 2008; 72:327-334.
24. Haasbeek C J, Slotman B J, Senan S. Radiotherapy for lung cancer: Clinical impact of recent technical advances. *Lung Cancer* 2008.
25. Roy A E, Wells P. Volume definition in radiotherapy planning for lung cancer: how the radiologist can help. *Cancer Imaging* 2006; 6:116-123.
26. Daisne J F, Gregoire V. [Multimodalities imaging for target volume definition in radiotherapy]. *Bull Cancer* 2006; 93:1175-1182.
27. Halpin S F. Brain imaging using multislice CT: a personal perspective. *British Journal of Radiology* 2004; 77 Spec No 1:S20-26.
28. Park I, Tamai G, Lee M C, et al. Patterns of recurrence analysis in newly diagnosed glioblastoma multiforme after three-dimensional conformal radiation therapy with respect to pre-radiation therapy magnetic resonance spectroscopic findings. *Int J Radiat Oncol Biol Phys* 2007; 69:381-389.
29. Treuer H, Kocher M, Hoevels M, et al. Impact of target point deviations on control and complication probabilities in stereotactic radiosurgery of AVMs and metastases. *Radiother Oncol* 2006; 81:25-32.
30. Bolondi L, Gaiani S, Celli N, et al. Characterization of small nodules in cirrhosis by assessment of vascularity: the problem of hypovascular hepatocellular carcinoma. [see comment]. *Hepatology* 2005; 42:27-34.
31. Dawson L A, Brock K K, Kazanjian S, et al. The reproducibility of organ position using active breathing control (ABC) during liver radiotherapy. 2001; 51:1410-1421.
32. Dawson L A, Ten Haken R K, Lawrence T S. Partial irradiation of the liver. *Semin Radiat Oncol* 2001; 11:240-246.
33. Funama Y, Awai K, Miyazaki O, et al. Improvement of low-contrast detectability in low-dose hepatic multidetector computed tomography using a novel adaptive filter: evaluation with a computer-simulated liver including tumors. 2006; 41:1-7.
34. Padhani A R, Ollivier L. The RECIST (Response Evaluation Criteria in Solid Tumors) criteria: implications for diagnostic radiologists. *Br J Radiol* 2001; 74:983-986.
35. Miles K A, Charnsangavej C, Lee F T, et al. Application of CT in the investigation of angiogenesis in oncology. *Acad Radiol* 2000; 7:840-850.
36. Tateishi U, Nishihara H, Watanabe S, et al. Tumor angiogenesis and dynamic CT in lung adenocarcinoma: radiologic-pathologic correlation. *J Comput Assist Tomogr* 2001; 25:23-27.
37. Choi J B, Park C K, Park D W, et al. Does contrast enhancement on CT suggest tumor response for chemotherapy in small cell carcinoma of the lung? *J Comput Assist Tomogr* 2002; 26:797-800.
38. Sahani D V, Kalva S P, Hamberg L M, et al. Assessing tumor perfusion and treatment response in rectal cancer with multisection CT: initial observations. *Radiology* 2005; 234:785-792.
39. Hermans R, Meijerink M, Van den Bogaert W, et al. Tumor perfusion rate determined noninvasively by dynamic computed tomography predicts outcome in head-and-neck cancer after radiotherapy. *Int J Radiat Oncol Biol Phys* 2003; 57:1351-1356.
40. Millar B A, Purdie T G, Yeung I, et al. Assessing perfusion changes during whole brain irradiation for patients with cerebral metastases. *J Neurooncol* 2005; 71:281-286.
41. Henderson E, Milosevic M F, Haider M A, et al. Functional CT imaging of prostate cancer. *Phys Med Biol* 2003; 48:3085-3100.
42. Ma S H, Xu K, Xiao Z W, et al. Peripheral lung cancer: relationship between multi-slice spiral CT perfusion imaging and tumor angiogenesis and cyclin D1 expression. *Clinical Imaging* 2007; 31:165-177.
43. Kiessling F, Boese J, Corvinus C, et al. Perfusion CT in patients with advanced bronchial carcinomas: a novel chance for characterization and treatment monitoring? *Eur Radiol* 2004; 14:1226-1233.
44. Haider M A, Milosevic M, Fyles A, et al. Assessment of the tumor microenvironment in cervix cancer using dynamic contrast enhanced CT, interstitial fluid pressure and oxygen measurements. *Int J Radiat Oncol Biol Phys* 2005; 62:1100-1107.
45. Harvey C J, Blomley M J, Dawson P, et al. Functional CT imaging of the acute hyperemic response to radiation therapy of the prostate gland: early experience. *Journal of Computer Assisted Tomography* 2001; 25:43-49.
46. Harvey C, Dooher A, Morgan J, et al. Imaging of tumour therapy responses by dynamic CT. *Eur J Radiol* 1999; 30:221-226.
47. Bondestam S, Halavaara J T, Jaaskelainen J E, et al. Perfusion CT of the brain in the assessment of flow alterations during brachytherapy of meningioma. *Acta Radiol* 1999; 40:469-473.
48. Roberts H C, Dillon W P. MR imaging of brain tumors: toward physiologic imaging. *AJNR Am J Neuroradiol* 2000; 21:1570-1571.
49. Roberts H C, Roberts T P, Brasch R C, et al. Quantitative measurement of microvascular permeability in human brain tumors achieved using dynamic contrast-enhanced MR imaging: correlation with histologic grade. *AJNR Am J Neuroradiol* 2000; 21:891-899.
50. Roberts H C, Roberts T P, Bollen A W, et al. Correlation of microvascular permeability derived from dynamic contrast-enhanced MR imaging with histologic grade and tumor labeling index: a study in human brain tumors. *Acad Radiol* 2001; 8:384-391.
51. Roberts H C, Roberts T P, Ley S, et al. Quantitative estimation of microvascular permeability in human brain 52. Kassner A, Roberts T P. Beyond perfusion: cerebral vascular reactivity and assessment of microvascular permeability. *Top Magn Reson Imaging* 2004; 15:58-65.
53. Kassner A, Roberts T, Taylor K, et al. Prediction of hemorrhage in acute ischemic stroke using permeability MR imaging. *AJNR Am J Neuroradiol* 2005; 26:2213-2217.
54. Lee KSSLaT-Y. An Adiabatic Approximation to the Tissue Homogeneity Model for Water Exchange in the Brain: II. Experimental Validation. *Journal of Cerebral Blood Flow & Metabolism* 1998:1378.
55. Roberts H C, Roberts T P, Smith WS, et al. Multisection dynamic CT perfusion for acute cerebral ischemia: the "toggling-table" technique. *AJNR Am J Neuroradiol* 2001; 22:1077-1080.
56. Kamena A, Streitparth F, Grieser C, et al. Dynamic perfusion CT: optimizing the temporal resolution for the calculation of perfusion CT parameters in stroke patients. *Eur J Radiol* 2007; 64:111-118.
57. Miles K A, Griffiths M R. Perfusion CT: a worthwhile enhancement? *Br J Radiol* 2003; 76:220-231.
58. Miles K A, Griffiths M R, Fuentes M A. Standardized perfusion value: universal CT contrast enhancement scale that correlates with FDG PET in lung nodules. *Radiology* 2001; 220:548-553.
59. Seppenwoolde Y, Shirato H, Kitamura K, et al. Precise and real-time measurement of 3D tumor motion in lung due to breathing and heartbeat, measured during radiotherapy. *Int J Radiat Oncol Biol Phys* 2002; 53:822-834.
60. Huda W, Scalzetti E M, Levin G. Technique factors and image quality as functions of patient weight at abdominal CT. *Radiology* 2000; 217:430-435.
61. Miles K A. Perfusion CT for the assessment of tumour vascularity: which protocol? *Br J Radiol* 2003; 76 Spec No 1:S36-42.
62. Miles K A, Young H, Chica S L, et al. Quantitative contrast-enhanced computed tomography: is there a need for system calibration? *Eur Radiol* 2007; 17:919-926.
63. Miles K A 2003 Perfusion CT for the assessment of tumour vascularity: which protocol? *Br J Radiol* 76 Spec No 1:S36-4
64. Koh T S, Markus Tan C K, and Tchoyoson Lim C C. 2006 Cerebral perfusion mapping using a robust and efficient method for deconvolution analysis of dynamic contrast-enhanced images. NeuroImage 32 643-65.
65. Asscher et al. (1965). Capillary permeability to plasma proteins. *Postgrad Med. J.* 41:425434.

The invention claimed is:

1. A phantom for simulation of perfusion, for use in dynamic flow imaging, the phantom comprising:
a first compartment having a first inlet and a first outlet, the first inlet being connectable to fluid source for introducing fluid into the phantom;
a second compartment having a second outlet;
wherein the first and the second compartments have fluid communication with each other, to simulate perfusion between the first and the second compartments;
each of the first and the second outlets being separately controllable to adjust outflow of fluid from each compartment and to adjust fluid pressure in each compartment, thereby controlling rates of communication of fluids between the first and the second compartments.

2. The phantom of claim 1 wherein at least a portion of the first compartment is contained in the second compartment.

3. The phantom of claim 2 wherein the first compartment has a plurality of orifices in the portion contained in the second compartment, for fluid communication with the second compartment.

4. The phantom of claim 2 wherein the first compartment is a tube.

5. The phantom of claim 1 wherein the second compartment has a second inlet.

6. The phantom of claim 1 wherein the first and the second compartments have fluid communication with each other at least via a plurality of orifices.

7. The phantom of claim 1 wherein the first and the second compartments have fluid communication with each other at least via a diffusion-based exchange mechanism.

8. The phantom of claim 1 wherein the first and the second compartments have fluid communication with each other at least via a microvascular exchange system.

9. A method of simulating perfusion in dynamic flow imaging using the phantom as defined in claim 1, the method comprising:
determining system parameters for controlling inflow and outflow of the phantom, to mimic a physiological condition;
configuring outlet valves according to the determined system parameters;
introducing a fluid into the phantom according to the determined system parameters; and
imaging output from the phantom.

10. The method of claim 9 wherein the physiological condition is that of a physiological organ.

11. The method of claim 10 wherein the physiological organ is a human liver or a human brain.

12. A system for simulation of perfusion, for use in dynamic flow imaging, the system comprising:
a phantom comprising:
a first compartment having a first inlet and a first outlet, the first inlet being connectable to fluid source for introducing fluid into the phantom;
a second compartment having a second outlet;
wherein the first and the second compartments have fluid communication with each other, to simulate perfusion between the first and the second compartments;
each of the first and the second outlets being separately controllable to adjust outflow of fluid from each compartment and to adjust fluid pressure in each compartment, thereby controlling rates of communication of fluids between the first and the second compartments;
a pump for providing fluid to the phantom;
an injector for providing contrast to the fluid; and
respective valves for controlling outflow from each of the first and the second outlets.

* * * * *